United States Patent [19]

Schnur

[11] 4,423,233

[45] Dec. 27, 1983

[54] HYPOGLYCEMIC 5-SUBSTITUTED OXAZOLIDINE-2,4-DIONES

[75] Inventor: Rodney C. Schnur, Groton, Conn.

[73] Assignee: Pfizer Inc., New York, N.Y.

[21] Appl. No.: 353,777

[22] Filed: Mar. 1, 1982

Related U.S. Application Data

[60] Division of Ser. No. 252,961, Apr. 23, 1981, Pat. No. 4,332,952, which is a continuation-in-part of Ser. No. 173,206, Jul. 28, 1980, abandoned.

[51] Int. Cl.³ .................... C07D 333/00; A61K 31/44
[52] U.S. Cl. ......................................... 549/58; 549/65; 549/75; 549/467; 549/479; 549/491; 424/258; 424/263
[58] Field of Search ................. 549/58, 65, 75, 467, 549/479, 491

[56] References Cited

U.S. PATENT DOCUMENTS

| | | | |
|---|---|---|---|
| 2,338,220 | 1/1944 | Wallingford | 260/307 |
| 2,721,197 | 10/1955 | Sheehan | 260/239.1 |
| 4,116,974 | 9/1978 | Farge et al. | 549/65 |
| 4,220,787 | 9/1980 | Scholz | 548/226 |
| 4,332,952 | 6/1982 | Schnur | 424/263 |
| 4,342,771 | 8/1982 | Schnur | 424/263 |

OTHER PUBLICATIONS

Clark-Lewis, Chem. Rev. 58, pp. 63-99 (1958).

*Primary Examiner*—Alan Siegel
*Attorney, Agent, or Firm*—Charles J. Knuth; Albert E. Frost; Robert K. Blackwood

[57] ABSTRACT

Hypoglycemic 5-furyl and 5-thienyl derivatives of oxazolidine-2,4-dione and the pharmaceutically-acceptable salts thereof; certain 3-acylated derivatives thereof; and intermediates useful in the preparation of said compounds.

16 Claims, No Drawings

HYPOGLYCEMIC 5-SUBSTITUTED OXAZOLIDINE-2,4-DIONES

CROSS REFERENCE TO RELATED APPLICATION

This application is a division of application Ser. No. 252,961, filed Apr. 23, 1981, now U.S. Pat. No. 4,332,952, which is a continuation-in-part of application Ser. No. 173,206, filed July 28, 1980, now abandoned, which is also the parent of application Ser. No. 222,202, filed Jan. 2, 1981 and the grandparent of co-pending application Ser. No. 252,962, filed Apr. 23, 1981, now U.S. Pat. No. 4,342,771.

BACKGROUND OF THE INVENTION

The present invention relates to certain novel 5-thienyl and 5-furyl derivatives of oxazolidine-2,4-dione having utility as hypoglycemic agents.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in a high percentage of diabetics where available synthetic hypoglycemic agents are not effective, requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Where effective, a synthetic hypoglycemic agent is preferred over insulin, being more convenient to administer and less prone to cause severe hypoglycemic reactions. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057-1080].

The 5-thienyloxazolidine-2,4-diones and 5-furyloxazolidine-2,4-diones of the present invention are novel, in spite of the fact that the oxazolidine-2,4-diones are broadly known as a class of compounds [for an extensive review, see Clark-Lewis, Chem. Rev. 58, pp. 63-99 (1958)]. Among the compounds known in this class are 5-phenyloxazolidine-2,4-dione, variously reported as an intermediate to certain beta-lactam antibacterial agents (Sheehan, U.S. Pat. No. 2,721,197), as an antidepressant agent (Plotnikoff, U.S. Pat. No. 3,699,229) and as an anticonvulsant agent [Brink and Freeman, J. Neuro. Chem. 19 (7), pp. 1783-1788 (1972)]; a number of 5-phenyloxazolidine-2,4-diones substituted on the phenyl ring, e.g., 5-(4-methoxyphenyl)oxazolidine-2,4-dione [King and Clark-Lewis, J. Chem. Soc., pp. 3077-3079 (1961)], 5-(4-chlorophenyl)oxazolidine-2,4-dione [Najer et al., Bull. soc. chim. France, pp. 1226-1230 (1961)], 5-(4-methylphenyl)oxazolidine-2,4-dione [Reibsomer et al., J. Am. Chem. Soc. 61, pp. 3491-3493 (1939)], and 5-(4-aminophenyl)oxazolidine-2,4-dione (German Pat. No. 108,026); and 5-(2-pyrryl)oxazolidine-2,4-dione [Ciamacian and Silber, Gazz. chim. ital. 16, 357 (1886); Ber. 19, 1708-1714 (1886)]. We have discovered, as disclosed hereinafter, that some of these compounds also possess hypoglycemic activity. However, to the converse, in the form of one of the preferred embodiments of the present invention, viz., 5-(3-thienyl)oxazolidine-2,4-dione, no anticonvulsant activity was noted, as measured following pentylenetetrazole or electroshock challenge. Furthermore, no antidepressant activity has been noted for this compound; rather, at doses higher than those at which it has hypoglycemic activity, this compound has been found to have depressant activity.

Oxazolidine-2,4-dione and substituted oxazolidine-2,4-diones (specifically, the 5-methyl and 5,5-dimethyl derivatives) have been reported as acid moieties suitable for forming acid-addition salts with the hypoglycemic, basic biguanides (Shapiro and Freedman, U.S. Pat. No. 2,961,377). We have determined that neither oxazolidine-2,4-dione itself, nor 5,5-dimethyloxazolidine-2,4-dione possess the hypoglycemic activity of the compounds of the present invention.

Recently, a group of spiro-oxazolidine-2,4-dione derivatives have been reported which are aldose reductase inhibitors, thus finding utility in the treatment of certain complications of diabetes (Schnur, U.S. Pat. No. 4,200,642).

Certain of the processes disclosed herein are the subject of a co-pending application by Rajeckas and Holland, Ser. No. 172,499, filed July 28, 1980, concurrently with the parent of the present application.

SUMMARY OF THE INVENTION

The present invention is concerned with compounds of the formulae

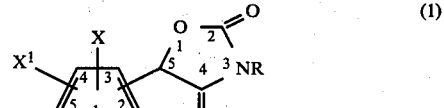

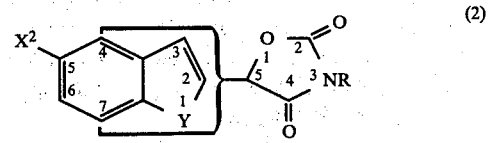

wherein
R is hydrogen, (C₁-C₄)-alkanoyl (e.g. formyl, acetyl, isobutyryl), benzoyl, (C₂-C₄)-carbalkoxy (e.g. carbomethoxy, carbethoxy, carboisopropoxy), (C₁-C₃)-alkylcarbamoyl (e.g., N-methylcarbamoyl, N-propylcarbamoyl), or di-(C₁-C₃)-dialkylcarbamoyl (e.g., N,N-dimethylcarbamoyl);
Y is sulfur or oxygen;
X is hydrogen, fluoro, chloro, bromo, iodo, methyl, phenyl, benzoyl or (C₁-C₃)-alkoxy;
X¹ is hydrogen or methyl; and
X² is hydrogen, fluoro, chloro, bromo or iodo; and the pharmaceutically acceptable cationic salts thereof when R is hydrogen.

When $X^1$ is hydrogen, the formula (1) is intended to encompass the full gamut of 5-(2-furyl)-, 5-(3-furyl)-, 5-(2-thienyl)- and 5-(3-thienyl)-derivatives of oxazolidine-2,4-dione wherein the substituent X can be attached to any vacant carbon position of the furan/thiophene ring, i.e.,

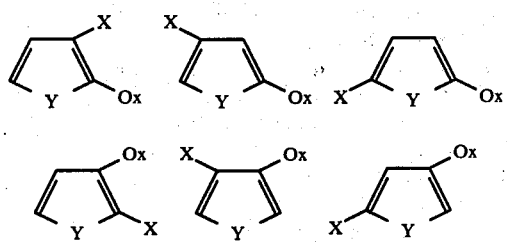

where X and Y are as defined above and Ox is used as an abbreviation for the oxazolidin-2,4-dione ring attached at the 5-position. When both X and $X^1$ are other than hydrogen, the second substituent can be inserted at either vacant position in any one of these six variants.

The formula (2) is intended to encompass those compounds wherein the oxazolidine is substituted at the 2-, 3- or 7-position of the benzo[b]furan/benzo[b]thiophene ring system, i.e.

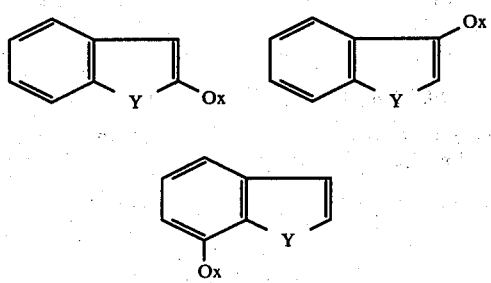

It is believed that the inherent, high activity of these compounds resides primarily in those compounds wherein R is hydrogen, and that those compounds wherein R is one of a variety of carbonyl derivatives defined above represent so-called pro-drugs, i.e.; the carbonyl side chain is removed by hydrolysis under physiological conditions, yielding the fully-active compound wherein R is hydrogen.

The expression "pharmaceutically acceptable cationic salts" is intended to define such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc.

The compounds of the present invention possess hypoglycemic activity, reflecting their clinical utility in the lowering of the blood glucose level of hyperglycemic mammals, including man, to normal values. They have the special advantage of lowering blood glucose values to a normal range without danger of causing hypoglycemia. The compounds of the present invention are tested for hypoglycemic (anti-hyperglycemic) activity in rats, using the so-called glucose tolerance test, as described in greater detail hereinafter.

Preferred compounds are those wherein R is hydrogen, or the pharmaceutically acceptable salts thereof. Among the thiophene derivatives [formula (1), Y is sulfur], the most preferred compounds, because of their excellent hypoglycemic activity, are the 3-thienyl, 4-halo-3-thienyl (particularly 4-bromo-3-thienyl), 4-alkoxy-3-thienyl (particularly 4-ethoxy-3-thienyl), 4-alkoxy-2-methyl-3-thienyl (particularly 4-ethoxy-2-methyl-3-thienyl and 4-methoxy-2-methyl-3-thienyl), 3-methyl-2-thienyl and 3-methoxy-2-thienyl analogs. Among the furan derivatives [formula (1), Y is oxygen] the 3-furyl, 2-furyl, 3-bromo-2-furyl and 5-chloro-2-furyl analogs are most preferred, particularly the 3-furyl analog. Among the benzo[b]furan/benzo[b]thiophene compounds [formula (2)], the 7-substituted analogs are preferred, especially the 5-chloro-7-benzo[b]furanyl compound.

DETAILS OF THE INVENTION

The compounds of the present invention are prepared by a variety of methods, as summarized in Flowsheet I, wherein
$R^1$ is

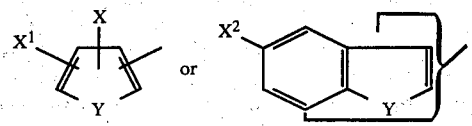

wherein X, $X^1$, $X^2$ and Y and positions of substitution are as defined above;
$R^2$ is lower alkyl (e.g. methyl or ethyl);
$R^3$ is hydrogen, lower alkyl or phenyl; and
$R^4$ is hydrogen, or acyl such as acetyl or benzoyl.

A particularly convenient synthesis for compounds of the present invention is via carboximidate (3). The latter compound is reacted with phosgene in an inert solvent such as tetrahydrofuran in the presence of 2 to 2.3 equivalents of a tertiary amine (e.g. triethylamine, N-methylmorpholine). A further equivalent of tertiary amine is used if the carboximidate is introduced as the acid addition salt (e.g. hydrochloride salt). The temperature of the reaction is not critical, but lower temperatures (e.g. −10° to 10° C.) are preferred during the initial stages of the reaction, particularly if it is desired to isolate the intermediate 4-alkoxyoxazol-2-one (4). Isolation of this intermediate is carried out by simple evaporation of the reaction mixture to dryness. On further reaction at higher temperatures (e.g. 20°–50° C.) or on aqueous work-up the intermediate (4) is converted to the desired oxazolidine-2,4-dione.

Flowsheet I
Oxazolidine-2,4-dione Precursors

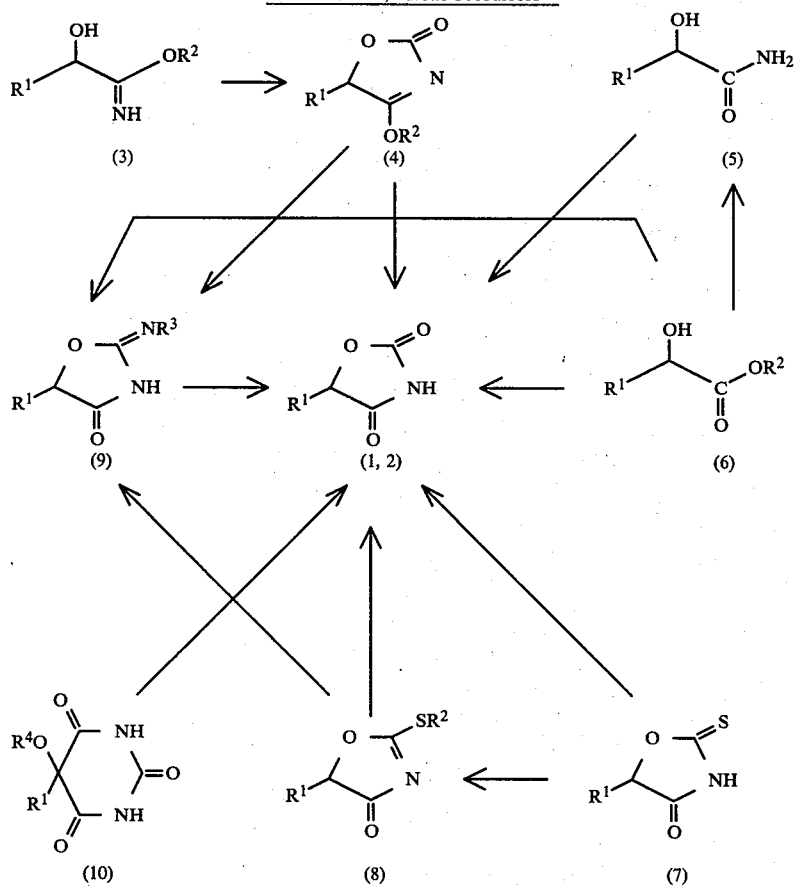

The carboximidate (3) is conveniently prepared from the corresponding aldehyde by the sequence:

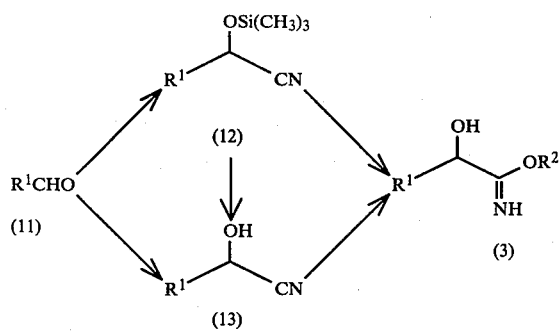

The aldehyde (11) is converted to the cyanohydrin (13) by standard procedures (e.g. via the bisulfite adduct, which is reacted with cyanide in a two phase, aqueous-organic solvent system). Alternatively, the aldehyde is converted to the trimethylsilyl cyanohydrin (12) by reaction with trimethylsilylcarbonitrile in the presence of a catalytic quantity of a Lewis acid, e.g., zinc iodide. A reaction inert solvent (e.g. methylene chloride, ether) is generally used when the aldehyde is a solid, but is optional when the aldehyde is a liquid. The temperature of the reaction is not critical, it being conveniently made up at reduced temperature (e.g. 0°–5° C.) and allowed to proceed at room temperature for a matter of hours or days, as necessary to achieve complete reaction. If desired, the trimethylsilyl ether can be hydrolyzed to cyanohydrin, conveniently at reduced temperature (e.g. −10° C.) in a two phase strong aqueous acid/organic solvent system.

Either the cyanohydrin (13) or the trimethylsilyl ether (12) is converted to the carboximidate (3) by strong acid catalyzed alcoholysis (using strictly anhydrous conditions). A convenient method is to simply dissolve the nitrile in alcohol which has been saturated with hydrogen chloride) and allow the solution to stand until carboximidate formation is complete. Temperature is not critical, although lower temperatures (e.g. 0°–25° C.) generally lead to more optimal yields.

The aldehydes required for the above syntheses are broadly available either commercially, or by literature methods, such as Rosenmund hydrogenation of the corresponding acid chloride [e.g. 3-furaldehyde; Hayes, J. Am. Chem. Soc. 71, 2581 (1949)], from halomethyl compounds by the Sommelet reaction [e.g. 3-thenaldehyde; Campaigne and LaSuer, J. Am. Chem. Soc. 70, 1557 (1948)], formylation [e.g. 2-thenaldehyde, 3-methyl-2-thenaldehyde, 5-methyl-2-thenaldehyde; Watson and Michaels, J. Am. Chem. Soc. 72, 1422 (1950), Organic Syntheses 31, 108 (1951); 3-bromo-2-thenaldehyde; Elliott et al., J. Chem. Soc. (C), 2551 (1971)]; reduction of chloromethyl substituted aldehydes [e.g. 5-methyl-2-furaldehyde, Spence and Wild, J. Chem. Soc., 338 (1935)], oxidation of the corresponding alcohol [e.g. 2-thenaldehyde; Emerson and Patrick, J. Org.

Chem., 14, 790 (1949)], interaction of Grignard reagents with orthoformic esters [e.g. 2-thenaldehyde; Cagniant, Bull. soc. chim. France 16, 849 (1949)], decarboxylation of alpha-keto acids [e.g. 2-thenaldehyde; Barger and Easson, J. Chem. Soc., 2100 (1938)], and halogenation [e.g. 2-bromo-3-thenaldehyde; Elliot et al., loc. cit.].

Another suitable precursor for the oxazolidine-2,4-diones of the present invention is the alpha-hydroxy amide (5). The latter compound is converted to the desired oxazolidine-2,4-dione (1, 2) either by reaction with alkyl chloroformate in the presence of a basic catalyst such as potassium carbonate, or by reaction with a dialkyl carbonate in the presence of a more strongly basic catalyst such as sodium methoxide or potassium tert-butoxide. An alcohol is generally suitable as solvent for the latter reaction with 1 to 3 equivalents of both dialkyl carbonate and base employed, preferably 2-3 equivalents of each.

The required alpha-hydroxy amide is conveniently prepared from cyanohydrin (13) or from alpha-hydroxy acid or ester (6):

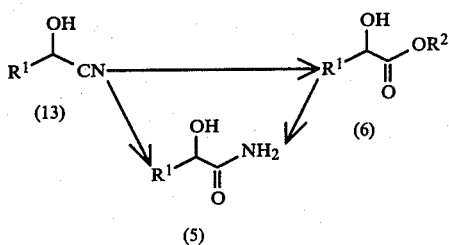

Convenient conditions for the hydrolysis of the cyanohydrin (13) are to treat the cyanohydrin in formic acid with excess concentrated hydrochloric acid. A temperature range of 0°-75° C. is generally satisfactory, depending upon the stability of the individual amide in this medium. If desired, an intermediate formate ester of (5) can be isolated under these conditions. Over hydrolysis to the acid can be avoided by tlc monitoring of the reaction, as detailed below. Convenient conditions for the aminolysis of ester (6) are to simply heat the ester in hot concentrated ammonium hydroxide.

The alpha-hydroxy ester (6) itself can also be employed as the immediate precursor of the desired oxazolidine-2,4-dione. The ester is reacted with urea (or one of certain substituted ureas, such as phenyl urea or 1-acetyl-3-methylurea) in the presence of a basic catalyst such as sodium ethoxide (suitably 1 equivalent) in alcohol at a temperature of 50°-110° C. The ester to be used for this purpose is by no means restricted to a simple lower alkyl ester, but can be any one of a broad variety of esters, e.g. phenyl, benzyl, etc. Furthermore, the ester can be replaced by a 1,3-dioxolan-4-one, e.g.,

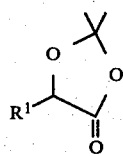

and the urea can be replaced by a urethan.

Two other precursors suitable for the synthesis of the desired oxazolidine-2,4-diones are the thio compounds (7) and (8). The 2-thioxo compound (7) is converted to the desired oxazolidine-2,4-diones under oxidative conditions, e.g. mercuric ion, aqueous bromine or chlorine, or aqueous hydrogen peroxide, usually in excess and in the presence of a co-solvent, such as a lower alcohol. The temperature of reaction is not critical, temperatures in the range 25°-100° C. generally satisfactory. The oxazolidine-2,4-diones are obtained from the alkylthio compounds (8) by simple acid or base catalyzed hydrolysis. Preferable conditions are aqueous hydrochloric acid in a temperature range of 0°-50° C.

The precursor 2-thioxo compound (7) is prepared from the corresponding aldehyde (11), generally accomplished in an aqueous acidic media by the action of thiocyanate (1-1.1 equivalents) and cyanide (1 to 1.2 equivalents) at 0°-70° C., following the method of Lindberg and Pederson by which method the preparation of 5-(2-thienyl)-2-thioxooxazolidin-4-one has been reported [Acta Pharm. Suecica 5 (1), pp. 15-22 (1968); Chem. Abstr. 69, 52050k]. The precursor 2-alkylthio compounds (8) can be prepared by alkylation of the 2-thioxo compounds (7), e.g. with an alkyl halide or dialkyl sulfate, preferably in the presence of at least two equivalents of a base such as alkoxide in a reaction inert solvent such as an alkanol. The 3-alkyl derivative can be a by-product of this reaction.

Also suitable as a precursor is the 2-iminooxazolidine-4-one derivative (9), readily hydrolyzed to the oxazolidine-2,4-dione, preferably under aqueous acid conditions. The required 2-iminooxazolidin-4-one is obtained by condensation of the alpha-hydroxy ester (6) with guanidine or with thiourea in the presence of one equivalent of a strong base such as sodium alkoxide, by ammonolysis of the 2-alkoxy compound (isomeric with 4) or the 2-thioalkyl compound (8), by alkali induced cyclization of the appropriate alpha-halogenureides ($R^1$CHZCONHCONH$R^3$ wherein Z is a halogen such as chloro or bromo), or by the condensation of the appropriate alkyl alpha-haloacetates ($R^1$CHZCOO$R^2$) with urea or a substituted urea ($R^3$NHCONH$_2$).

Ammonolysis of the 4-alkoxy derivatives (4) yields 4-imino derivatives (isomeric with 9). The latter compounds are also readily hydrolyzed to oxazolidine-2,4-diones. The 4-alkoxy derivatives themselves are also prepared from the silver salt of the desired oxazolidine-2,4-dione.

Also highly useful as precursors of the oxazolidine-2,4-diones of the present invention are the dialuric acids and acyl dialuric acids (10). These are readily converted, under mildly basic conditions, to the desired oxazolidine-2,4-diones. Methods suitable for the preparation of precursor dialuric acids (10) are shown in Flowsheet II, wherein the substituents $R^1$, $R^2$ and $R^4$ are as defined above, and M is Li, MgCl, MgBr, MgI, or other suitable metal.

A general method for preparing dialuric acids appropriate as precursors of the oxazolidine-2,4-diones of the present invention is from the malonic ester derivatives (14), involving the two stages of base catalyzed condensation with urea and oxidation to the hydroxy or acyloxy compound. When the first stage is oxidation, the intermediate is a so-called tartronic acid derivative (15), while when the first stage is condensation, the intermediate is a so-called barbituric acid (16). When $R^1$ is thienyl or benzo[b]thienyl, it is preferred to carry out oxidation as the first stage, preventing possible complications of nitrogen oxidation. When condensation is the second stage, the dialuric acid is usually not isolated, at least in pure form, and is further converted, under basic conditions of the condensation, to the oxazolidine-2,4-dione.

Flowsheet II

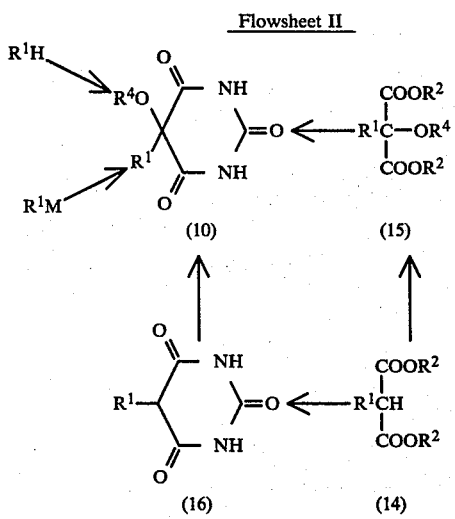

The substituted malonic esters required for the above syntheses, when not available commercially, are obtained by literature methods, such as alcoholysis of alpha-cyano esters [cf. Steele, J. Am. Chem. Soc. 53, 286 (1931)], carbalkoxylation of esters [cf. Horning and Finelli, Org. Syntheses 30, 43 (1950)] and decarbonylation of alpha-keto esters obtained by the condensation of dialkyl oxalate with carboxylate esters [Reichstein and Morsman, Helv. Chim. Acta 17, 1123 (1934)]; Blicke and Zienty, J. Am. Chem. Soc. 63, 2946 (1941)].

A less general method for the preparation of the appropriate dialuric acid intermediate is to react an electron rich heteroaryl/aryl compound, e.g. methoxyfuran/methoxythiophene, with alloxan hydrate. For example:

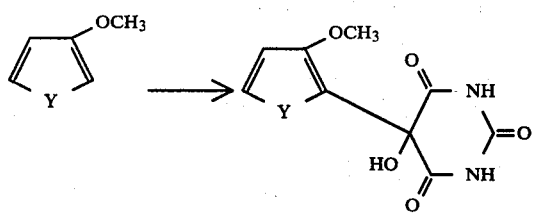

Now available is yet another broadly applicable method, preferred when the appropriate starting materials are readily available, which involves the reaction of alloxan (preferably in anhydrous form) with the appropriate organometal derivative (e.g. organolithium, Grignard reagent). Protection strategies are required when using this method for preparation of certain oxazolidine-2,4-diones wherein the substituent X is not compatible with organometallic reactions, e.g. when X is benzoyl it is protected as its ethylenic ketal.

The furan/thiophene derivatives required for the latter syntheses proceeding via alloxan are available commercially or by literature methods.

It will be evident to those skilled in the art that the preferred process for the oxazolidine-2,4-diones of the present invention will vary from one given value of $R^1$ to another, depending upon such factors as availability of starting materials, yields, ability to remove undesirable impurities from the end-products, the chemical nature of the substituent groups contained in the final products, etc.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

3-Acylated derivatives of the present invention are readily prepared by using standard conditions of acylation, e.g. the reaction of the oxazolidine-2,4-dione salt (per se, or conveniently formed in situ by the addition of one equivalent of a tertiary amine such as triethylamine or N-methylmorpholine with an equivalent of the appropriate acid chloride or acid anhydride) or reaction of the oxazolidine-2,4-dione with the appropriate organic isocyanate, optionally in the presence of a catalytic amount of a tertiary amine base. In either case, the reaction is carried out in a reaction inert solvent, such as toluene, tetrahydrofuran or methylene chloride. The temperature is not critical, and can be over a broad range (e.g. 0°–150° C.).

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

The oxazolidine-2,4-diones of the present invention are readily adapted to clinical use as antidiabetic agents. The hypoglycemic activity required for this clinical use is defined by the glucose tolerance test procedure which follows. Intact male albino rats are the experimental test animals employed for such purposes. The test animals are fasted approximately 18–24 hours. The rats are weighed, numbered and recorded in groups of five or six as needed. Each group of animals is then dosed intraperitoneally with glucose (one gram per kilogram) and orally with either water (controls) or compound (at a level usually selected from the range 0.1 to 100 mg./kg.). Blood glucose levels (mg./100 ml.) are measured in tail blood samples over a period of 3 hours in both control and treated groups. With equivalent zero hour blood glucose levels in control and treated groups, the % lowering of blood glucose at 0.5 hour, 1 hour, 2 hours and 3 hours is calculated as:

$$\frac{[\text{Control Blood Glucose}] - [\text{Treated Blood Glucose}]}{[\text{Control Blood Glucose}]} \times 100\%$$

Clinically useful hypoglycemic agents show activity in this test. The hypoglycemic activities determined for compounds of the present invention are summarized in Table I. This table records % blood glucose lowering at the 0.5 hour and 1 hour time points. A blood glucose lowering of 9% or greater generally reflects statistically significant hypoglycemic activity in this test. Those compounds which show significant activity only at the 2 hour or 3 hour points have such activity recorded in footnotes.

The oxazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg. body weight of the subject per day, preferably about 0.20 to about 20 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

TABLE I

Hypoglycemic Activity of Oxazolidine-2,4-Diones in the Rat Glucose Tolerance Test

| Ar | Dose (mg./kg.) | % Lowering Blood Glucose Level 0.5 hr. | 1 hr. |
|---|---|---|---|
| 2-Thienyl | 10 | 11 | 8 |
| 5-Benzoyl- | 25 | 10 | 7 |
| 3-Bromo- | 10 | 8 | 6(a) |
| 5-Bromo- | 100 | 36 | 19 |
| 5-Chloro- | 100 | 26 | 17 |
| 3-Methoxy- | 5 | 13 | 16 |
| 5-Methoxy- | 25 | 9 | 7 |
| 3-Methyl- | 100 | 30 | 17 |
|  | 10 | 14 | 12 |
| 5-Methyl | 50 | 18 | 10 |
| 5-Phenyl | 50 | 1 | 5(b) |
| 3-Thienyl | 10 | 23 | 20 |
|  | 5 | 20 | 17 |
| 4-Bromo- | 100 | 31 | 25 |
|  | 10 | 14 | 9 |
| 4-Methoxy- | 5 | 11 | 8 |
| 4-Methoxy-2-methyl- | 5 | 16 | 14 |
| 4-Ethoxy- | 5 | 19 | 19 |
| 4-Ethoxy-2-methyl- | 5 | 7 | 12 |
| 4-Propoxy- | 5 | 11 | 6 |
| 2-Furyl | 100 | 27 | 23 |
|  | 10 | 11 | 7 |
| 3-Bromo- | 25 | 18 | 10 |
|  | 5 | 11 | 11 |
| 5-Bromo- | 50 | 19 | 20 |
|  | 10 | 2 | 11 |
| 5-Chloro- | 25 | 21 | 20 |
| 3-Methoxy- | 25 | 10 | 10 |
| 5-Methyl- | 100 | 27 | 19 |
| 5-Phenyl- | 25 | 6 | 4(c) |
| 3-Furyl | 10 | 17 | 13 |
|  | 5 | 14 | 8 |
| 2,5-Dimethyl- | 100 | 33(e) | 16(f) |
| 4-Iodo- | 25 | 19(e) | 0(f) |

TABLE I-continued

Hypoglycemic Activity of Oxazolidine-2,4-Diones in the Rat Glucose Tolerance Test

| Ar | Dose (mg./kg.) | % Lowering Blood Glucose Level 0.5 hr. | 1 hr. |
|---|---|---|---|
| 3-Benzo[b]thienyl | 100 | 11 | 5 |
| 7-Benzo[b]thienyl | 100 | −4 | 12(d) |
| 7-Benzo[b]furanyl | — | — | — |
| 5-Chloro- | 10 | 23(e) | 10(f) |

(a)11 at 2 hours.
(b)9 at 2 hours.
(c)10 at 3 hours.
(d)16 at 2 hours; 10 at 3 hours.
(e)At 0.75 hours.
(f)At 1.5 hours.

The compounds can be used in pharmaceutical preparations containing the compound, or a pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions can if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intramuscular administration being preferred in man.

It will be evident to those skilled in the art that the compounds of the present invention are asymmetric and therefore capable of existing in two optically active enantiomeric forms. The racemic compounds of the present invention, being acids, form salts with organic amines. These racemic forms are therefore generally capable of resolution into the optically active forms by the classic method of forming diastereomeric salts with optically active amines, now separable by selective crystallization. In general, one of the enantiomeric forms is found to have greater activity than the other.

The present invention is illustrated by the following examples. However, it should be understood that the invention is not limited to the specific details of these examples.

EXAMPLE 1

2-(3-Furyl)-2-Trimethylsiloxyethanenitrile

To a mixture of 3-furaldehyde (1.92 g., 20 mmoles) and about 100 mg. of zinc iodide in 25 ml. of ether, trimethylsilylcarbonitrile (4.74 g., 48 mmoles) was added dropwise. The mixture was stirred about 16 hours at room temperature. The reaction mixture was washed sequentially with saturated sodium bicarbonate, water and brine, dried over anhydrous sodium sulfate, filtered and evaporated in vacuo to yield 2-(3-furyl)-2-trimethylsiloxyethanenitrile [2.2 g.; pnmr/CDCl$_3$/delta: 0.2 (s, 9H); 5.4 (s, 1H); 6.4 (m, 1H); 7.3 (m, 1H); 7.5 (m, 1H)].

EXAMPLE 2

Ethyl 1-Hydroxy-1-(3-furyl)methanecarboximidate Hydrochloride 2-(3-Furyl)-2-trimethylsiloxyethanenitrile (1.0 g.) was dissolved in 10 ml. of saturated ethanolic hydrogen chloride at 0°–5° C. The resulting solution was held at about 5° C. for 16 hours. The reaction mixture was concentrated to about half volume and diluted with ether. Filtration, with ether wash, gave ethyl 1-hydroxy-1-(3-furyl)methanecarboximidate hydrochloride (746 mg.; m.p. 113°–115° C.; m/e 169).

EXAMPLE 3

5-(3-Furyl)oxazolidine-2,4-dione

Ethyl 1-hydroxy-1-(3-furyl)methanecarboximidate hydrochloride (1.5 g., 7.5 mmoles) was combined with 50 ml. of tetrahydrofuran and triethylamine (2.21 g., 21.9 mmoles) and cooled to 10° C. Phosgene was bubbled through the cooled reaction mixture for 20 minutes. After stirring the mixture for an additional 30 minutes, nitrogen was flushed through the mixture for 10 minutes. The reaction mixture was poured slowly into 100 g. of crushed ice. The product was extracted into two portions of ether and crude product isolated as an oil by evaporation. The oil was taken up in 5 ml. of 1 N sodium hydroxide and extracted with ether. The basic aqueous phase was acidified and extracted with fresh ether. Product was isolated as a gummy solid (600 mg.) by evaporation of the latter ether extract. Trituration with chloroform afforded purified 5-(3-furyl)oxazolidine-2,4-dione (109 mg.; m.p. 86°–88° C.; m/e 167). Addition of hexane to the chloroform triturate gave a second crop of product (66 mg.; m.p. 86°–88° C., m/e 167).

Analysis: Calcd. for C$_7$H$_5$O$_4$N: C, 50.31; H, 3.01; N, 8.38. Found: C, 49.97; H, 3.13; N, 8.37.

EXAMPLE 4

2-(5-Chloro-2-furyl)-2-trimethylsiloxyethanenitrile

5-Chloro-2-furaldehyde (2.7 g., 21 mmoles) was dissolved in 30 ml. of ether. Trimethylsilylcarbonitrile (6.3 ml., 50 mmoles) and zinc iodide (about 50 mg.) were added and the mixture stirred for 1.5 hours at room temperature, at which time tlc (hexane:ethyl acetate 8:1) indicated complete reaction. Concentration to dryness afforded 2-(5-chloro-2-furyl)-2-trimethylsiloxyethanenitrile as an oil [5.5 g.; pnmr/CDCl$_3$/delta: 0.3 (s, 9H); 5.4 (s, 1H); 6.1 (d, 1H); 6.5 (d, 1H)].

EXAMPLE 5

Ethyl 1-(5-chloro-2-furyl)-1-hydroxymethanecarboximidate Hydrochloride 2-(5-Chloro-2-furyl)-2-trimethylsiloxyethanenitrile (2.3 g.) was dissolved in saturated ethanolic hydrogen chloride (25 ml.) at 0° C. The solution was held for 2.5 hours at about 5° C. and then concentrated to oil. Trituration with 20 ml. of ether afforded crystalline ethyl 1-(5-chloro-2-furyl)-1-hydroxymethanecarboximidate hydrochloride (1.2 g.; m.p. 112°–114° C.; m/e 203).

EXAMPLE 6

5-(5-Chloro-2-furyl)oxazolidine-2,4-dione

Ethyl 1-(5-chloro-2-furyl)-1-hydroxymethanecarboximidate hydrochloride (1.2 g., 5 mmoles) was suspended in 50 ml. of tetrahydrofuran and cooled in an ice bath. Following the addition of triethylamine (2.1 ml., 15 mmoles), phosgene was bubbled into the reaction mixture for 20 minutes, maintaining the temperature at 10° to 20 C. The mixture was flushed with nitrogen and poured slowly into 100 ml. of crushed ice. The quenched reaction mixture was extracted with 100 ml. of ether, and the ether back-extracted with brine and concentrated to an oil. The oil was taken up in 15 ml. of fresh ether, the solution clarified and extracted with 10 ml. of 1 N sodium hydroxide. The basic extract was acidified with concentrated hydrochloric acid and product extracted into ethyl acetate. After back extracting with water, the ethyl acetate layer was concentrated to an oil (550 mg.). A portion of this oil (500 mg.) was chromatographed on about 50 ml. of silica gel, with 5:1 hexane:ethyl acetate containing 5% acetic acid as eluant. The column was monitored by tlc (same eluant). Late eluted, product containing fractions were combined, evaporated to dryness and triturated with hexane, affording 5-(5-chloro-2-furyl)oxazolidine-2,4-dione [177 mg.; m.p. 112°–114° C.; m/e 201; R$_f$0.25 (5:1 hexane:ethyl acetate with 5% acetic acid)].

Analysis: Calcd. for C$_7$H$_4$O$_4$NCl: C, 41.71; H, 2.00; N, 6.95. Found: C, 41.80; H, 2.21; N, 6.77.

EXAMPLE 7

2-(5-Bromo-2-furyl)-2-trimethylsiloxyethanenitrile

5-Bromo-2-furaldehyde (1.1 g., 6 mmoles) was dissolved in 50 ml. of ether. A catalytic quantity (about 50 mg.) of zinc iodide was added and then trimethylsilylcarbonitrile (746 mg., 1.2 equiv.) was added dropwise. The reaction was monitored by ir (disappearance of typical carbonyl absorption) and pnmr (disappearance of typical aldehyde proton peak). After 60 minutes at room temperature, the reaction mixture was washed with saturated sodium bicarbonate, twice with water, and finally with brine, dried over anhydrous sodium sulfate and evaporated to yield 2-(5-bromo-2-furyl)-2-trimethylsiloxyethanenitrile as an oil [1.2 g.; pnmr/CDCl$_3$/delta: 0.3 (s, 9H); 5.6 (s, 1H); 6.4 (d, 1H); 6.6 (d, 1H)].

EXAMPLE 8

Ethyl 1-(5-Bromo-2-furyl)-1-hydroxymethanecarboximidate Hydrochloride

Following the procedure of Example 2, except that the reaction mixture was not concentrated prior to addition of ether, 2-(5-bromo-2-furyl)-2-trimethylsiloxyethanenitrile (1.2 g.) was converted to ethyl 1-(5-bromo-2-furyl)-1-hydroxymethanecarboximidate hydrochloride (480 mg., m.p. 120°–122° C., m/e 247, 249). A less pure second crop (235 mg., m.p. 104°–106° C.) was recovered by evaporation of mother liquor and trituration of the residue with ether.

EXAMPLE 9

5-(5-Bromo-2-furyl)oxazolidine-2,4-dione

Ethyl 1-(5-bromo-2-furyl)-1-hydroxymethanecarboximidate hydrochloride (982 mg., 3.4 mmoles) was converted to 5-(5-bromo-2-furyl)oxazolidine-2,4-dione [126 mg., m.p. 126°–129° C., m/e 245, 247, $R_f$ 0.2 (5:1 hexane:ethyl acetate with 5% acetic acid)] by the procedure of Example 3.

EXAMPLE 10

2-(3-Bromo-2-furyl)-2-trimethylsiloxyethanenitrile

By the procedure of Example 1, 3-bromo-2-furaldehyde (1.75 g., 10 mmoles) in 50 ml. of ether was reacted with trimethylsilylcarbonitrile (8.8 ml., 70 mmoles) in the presence of about 100 mg. of zinc iodide. At the end of the 16 hour reaction period, the ether supernatant was decanted from solids and evaporated to dryness to yield 2-(3-bromo-2-furyl)-2-trimethylsiloxyethanenitrile [3 g., $R_f$ 0.7 (3:1 hexane:ethyl acetate)].

EXAMPLE 11

Ethyl 1-(3-Bromo-2-furyl)-1-hydroxymethanecarboximidate Hydrochloride 2-(3-Bromo-2-furyl)-2-trimethoxysilylethanenitrile (6.8 g.) was dissolved in 70 ml. of saturated ethanolic hydrogen chloride at 0° C. and maintained at about 5° C. for 2 hours. Concentration to dryness and trituration with acetone afforded ethyl 1-(3-bromo-2-furyl)-1-hydroxymethanecarboximidate hydrochloride [4.4 g., m.p. 117°–119° (dec.)].

EXAMPLE 12

5-(3-Bromo-2-furyl)oxazolidine-2,4-dione

By the procedures of Example 6, except that phosgene was bubbled into the reaction mixture at 0° to 10° C., ethyl 1-(3-bromo-2-furyl)-1-hydroxymethanecarboximidate hydrochloride (4.4 g.) was converted to purified 5-(3-bromo-2-furyl)oxazolidine-2,4-dione [847 mg.; m.p. 128°–130° C.; $R_f$ 0.20 (5:1 hexane:ethyl acetate containing 5% acetic acid)].

Analysis: Calcd. for $C_7H_4O_4NBr$: C, 34.16; H, 1.63; N, 5.69. Found: C, 34.30; H, 1.88; N, 5.67.

EXAMPLE 13

2-(2-Furyl)-2-trimethylsiloxyethanenitrile

2-Furaldehyde (24 g., 0.25 mole) was cooled to 0°–5° C., zinc iodide (500 mg.) was added and the mixture stirred. Trimethylsilylcarbonitrile (30 ml.) was added dropwise. The mixture was allowed to warm to room temperature and stirred for approximately 64 hours at room temperature. The reaction mixture was diluted with methylene chloride, extracted twice with saturated sodium bicarbonate, dried over anhydrous magnesium sulfate, treated with activated carbon, filtered and evaporated to yield 2-(2-furyl)-2-trimethylsiloxyethanenitrile as an oil [36 g., 74%; pnmr/CDCl3/delta: 0.2 (s, 9H); 5.6 (s, 1H); 6.4 (m, 1H); 6.6 (m, 1H); 7.4 (d, 1H)].

EXAMPLE 14

Ethyl 1-(2-Furyl)-1-hydroxymethanecarboximidate

Following the procedure of Example 2, 2-(2-furyl)-2-trimethylsiloxyethanenitrile (15 g.) was reacted with saturated ethanolic hydrogen chloride, except that a reaction time of about two hours was employed. Crude product was isolated by evaporating the reaction mixture to an oil. The oil was partitioned in 400 ml. of chloroform and saturated sodium bicarbonate. The chloroform was washed twice with fresh saturated sodium bicarbonate, washed once with brine, dried over anhydrous magnesium sulfate, filtered and concentrated to yield ethyl 1-(2-furyl)-1-hydroxymethanecarboximidate as an oil [10.6 g., 81%; pnmr/CDCl3/delta: 1.3 (t, 3H); 4.1 (q, 2H); 5.1 (s, 1H); 4.8–5.2 (m, 1H); 6.3 (m, 2H); 7.3 (d, 1H)].

EXAMPLE 15

5-(2-Furyl)oxazolidine-2,4-dione

Ethyl 1-(2-furyl)-1-hydroxymethanecarboximidate (10.5 g., 6.2 mmoles) was dissolved in 125 ml. of stirring tetrahydrofuran and cooled to 0°–5° C. Triethylamine (12.5 g., 0.124 mole) was added and the cold solution then perfused with phosgene for 35 minutes, warmed to room temperature and stirred for an additional 16 hours. The reaction mixture was slowly poured into 1 liter of ice and water. The product was extracted into 3 portions of ethyl acetate. The extracts were combined and product extracted into 4 portions of 1 N sodium hydroxide. The combined aqueous extracts were acidified with 6 N hydrochloric acid, and product extracted into 4 portions of chloroform. The combined chloroform extracts were dried over anhydrous magnesium sulfate, treated with activated carbon, filtered and evaporated to yield crude product as an oil (2.1 g.). Column chromatography on 100 g. of silica gel with 2:1 chloroform:ethyl acetate as eluant in 10 ml. fractions, monitored by tlc, gave, by evaporation of fractions 36–48, purified 5-(2-furyl)oxazolidine-2,4-dione (281 mg.; m.p. 99°–102° C.; m/e 167). Recrystallization from toluene gave more highly purified product (235 mg., m.p. 101°–103° C.).

Analysis: Calcd. for $C_7H_5O_4N$: C, 50.31; H, 3.02; N, 8.38. Found: C, 50.41; H, 3.25; N, 8.28.

EXAMPLE 16

5-Hydroxy-5-(3-methoxy-2-furyl)-2,4,6(1H,3H,5H)-pyrimidinetrione

3-Methoxyfuran (3.5 g., approximately 50% pure from Preparation 10), alloxan hydrate [5,5-dihydroxy-2,4,6(1H,3H,5H)-pyrimidinetrione, 4.8 g.] and 75 ml. of ethanol were combined and refluxed for 1 hour. The reaction mixture was cooled to room temperature and concentrated to dryness. Trituration of the residue with 25 ml. of water afforded 5-hydroxy-5-(3-methoxy-2-furyl)-2,4,6(1H,3H,5H)-pyrimidinetrione [1.9 g., m.p. 120–130 (dec.), m/e 240].

EXAMPLE 17

5-(3-Methoxy-2-furyl)oxazolidine-2,4-dione

5-Hydroxy-5-(3-methoxy-2-furyl)-2,4,6(1H,3H,5H)-pyrimidinetrione (1.7 g.) was stirred with 1 N sodium hydroxide (14 ml., 14 mmoles) for 20 minutes. The reaction mixture was acidified with acetic acid and product extracted into ethyl acetate and isolated in crude form by evaporation to an oil. Chromatography on ca. 100 ml. of silica gel, monitored by tlc, afforded 5-(3-methoxy-2-furyl)oxazolidine-2,4-dione [470 mg., m.p. 102°–104° C., $R_f$ 0.6 (1:1 hexane:ethyl acetate with 5% acetic acid)].

EXAMPLE 18

2-(5-Phenyl-2-thienyl)-2-trimethylsiloxyethanenitrile

5-Phenyl-2-thenaldehyde (0.9 g.) in 35 ml. of ether was reacted with 1 ml. of trimethylsilylcarbonitrile in the presence of about 50 mg. of zinc iodide. After 1 hour of stirring at room temperature, tlc indicated reaction was complete. Evaporation to dryness gave 2-(5-phenyl-2-thienyl)-2-trimethylsiloxyethanenitrile [1.65 g., $R_f$ 0.5 (5:1 hexane:ethyl acetate with 5% acetic acid)].

EXAMPLE 19

Ethyl 1-Hydroxy-1-(5-phenyl-2-thienyl)methanecarboximidate Hydrochloride 2-(5-Phenyl-2-thienyl)-2-trimethylsiloxyethanenitrile (1.6 g.) was dissolved in 30 ml. of cold, saturated ethanolic hydrogen chloride and maintained at 0° to 5° C. for about 17 hours. The reaction mixture was evaporated to dryness and triturated with ethyl acetate to yield ethyl 1-hydroxy-1-(5-phenyl-2-thienyl)methanecarboximidate hydrochloride [0.9 g.; pnmr/DMSO/delta: includes 1.1 (3H); 4.0 (2H); 5.2 (1H); 6.5 (1H)].

EXAMPLE 20

5-(5-Phenyl-2-thienyl)oxazolidine-2,4-dione

Ethyl 1-hydroxy-1-(5-phenyl-2-thienyl)methanecarboximidate hydrochloride (790 mg., 2.6 mmoles) and triethylamine (1.4 ml., 10 mmoles) were reacted with phosgene and product isolated according to the procedures of Example 12, except that the eluant in the chromatography was 2:1 ethyl acetate:hexane, affording 5-(5-phenyl-2-thienyl)oxazolidine-2,4-dione (172 mg., m.p. 233°-235° C.).

Analysis: Calcd. for $C_{13}H_9O_3NS$: C, 60.23; H, 3.50; N, 5.40. Found: C, 59.94; H, 3.65; N, 5.38.

EXAMPLE 21

2-(2-Thienyl)-2-trimethylsiloxyethanenitrile

By the procedure of Example 13, 2-thenaldehyde (56.1 g., 46.8 ml., 0.5 mole) was reacted for 16 hours with trimethylsilylcarbonitrile (60 ml.) in the presence of zinc iodide (approximately 0.5 g.), yielding 2-(2-thienyl)-2-trimethylsiloxyethanenitrile as an oil [92 g.; m/e 211; pnmr/CDCl$_3$/delta: 0.2 (s, 9H); 5.8 (s, 1H); 6.9-7.5 (m, 3H)].

EXAMPLE 22

Ethyl 1-Hydroxy-1-(2-thienyl)methanecarboximidate 2-(2-Thienyl)-2-trimethylsiloxyethanenitrile (45 g.) was dissolved in 450 ml. of absolute ethanol. The solution was cooled to 0°-5° C. and perfused with hydrogen chloride for 40 minutes. The mixture was kept at about 5° C. for 16 hours and evaporated to dryness. The residue was triturated with four 200 ml. portions of ether, and then partitioned between 400 ml. of methylene chloride and saturated sodium bicarbonate. The organic phase was washed twice with saturated sodium bicarbonate, treated with activated carbon, filtered and concentrated to yield ethyl 1-hydroxy-1-(2-thienyl)methanecarboximidate as an oil which solidified on standing [10 g.; pnmr/CDCl$_3$/delta: 1.2 (t, 3H); 4.1 (q, 2H); 5.2 (s, 1H), 5.9 (s, 1H); 6.8-7.3 (m, 3H); 7.3-8.1 (s, 1H)].

EXAMPLE 23

5-(2-Thienyl)oxazolidine-2,4-dione

Ethyl 1-hydroxy-1-(2-thienyl)methanecarboximidate (10 g., 5.4 mmoles) and triethylamine (15.1 ml., 10.8 mmoles) were dissolved in 100 ml. of tetrahydrofuran. The solution was cooled to 0°-5° C. and perfused with phosgene for 45 minutes. Stirring was continued for an additional 5 hours at 0°-5° C. The reaction mixture was poured slowly over 1500 ml. of crushed ice. The product was extracted into 1.1 liter of ethyl acetate in three portions. The combined ethyl acetate extracts were then extracted twice with saturated sodium bicarbonate and once with 1:1 saturated sodium carbonate:water. The combined bicarbonate and carbonate washes were acidified to pH 1-2 with 6 N hydrochloric acid and product extracted into several portions of ether. The combined ether extracts were washed with brine, dried over anhydrous magnesium sulfate, treated with activated charcoal, filtered and evaporated to yield product (3.0 g.). Recrystallization from toluene afforded 5-(2-thienyl)oxazolidine-2,4-dione (1.8 g.; m.p. 138°-140° C., m/e 183).

Analysis: Calcd. for $C_7H_5NO_3S$: C, 45.89; H, 2.75; N, 7.65. Found: C, 45.99; H, 2.87; N, 7.62.

EXAMPLE 24

2-(3-Methyl-2-thienyl)-2-trimethylsiloxyethanenitrile

Following the procedure of Example 13, 3-methyl-2-thenaldehyde (31.6 g., 0.25 mole) was reacted with trimethylsilylcarbonitrile (30 ml.) for 16 hours in the presence of 500 mg. of zinc iodide. The reaction mixture was diluted with 200 ml. of methylene chloride and further isolated also according to Example 13, affording 2-(3-methyl-2-thienyl)-2-trimethylsiloxyethanenitrile [52 g., 93%; pnmr/CDCl$_3$/delta: 0.2 (s, 9H); 2.3 (s, 3H); 5.7 (s, 1H); 6.8 (d, 1H); 7.25 (d, 1H)].

EXAMPLE 25

Ethyl 1-Hydroxy-1-(3-methyl-2-thienyl)methanecarboximidate 2-(3-Methyl-2-thienyl)-2-trimethylsiloxyethanenitrile (13 g.) was added dropwise to 100 ml. of cold ethanol, saturated with hydrogen chloride, keeping the temperature at 0°-4° C. After 1 hour at 0°-4° C., the reaction mixture was evaporated to dryness. The residue was triturated three times with 100 ml. portions of ether, and then partitioned between 300 ml. of methylene chloride and saturated sodium bicarbonate. The separated methylene chloride layer was washed with two additional portions of saturated sodium bicarbonate, dried over anhydrous magnesium sulfate, filtered and evaporated to yield ethyl 1-hydroxy-1-(3-methyl-2-thienyl)methanecarboximidate (8.0 g., 69%; m.p. 73°-76° C.; m/e 199).

EXAMPLE 26

5-(3-Methyl-2-thienyl)oxazolidine-2,4-dione

Ethyl 1-hydroxy-1-(3-methyl-2-thienyl)methanecarboximidate (6.0 g., 0.03 mole) was dissolved in 75 ml. of tetrahydrofuran and cooled to 0°-5° C. Triethylamine (6.07 g., 8.37 ml., 0.06 mole) was added, the solution was perfused with phosgene for 35 minutes, and poured slowly into 1 liter of ice and water. The product was extracted into three portions of ethyl acetate. The ethyl acetate extracts were combined and product extracted into four portions of saturated sodium bicarbonate. The combined aqueous extracts were acidified with 6 N hydrochloric acid and product reextracted into 3 portions of fresh ethyl acetate. The combined fresh organic extracts were dried over anhydrous magnesium sulfate, filtered, and evaporated to yield product as an oil (2.4 g., 41%), which crystallized on scratching. Recrystallization from toluene gave purified 5-(3-methyl-2-thienyl)oxazolidine-2,4-dione (1.84 g., 31% overall; m.p. 119°–121° C., m/e 197).

Analysis: Calcd. for $C_8H_7O_3NS$: C, 48.72; H, 3.58; N, 7.10. Found: C, 48.65; H, 3.58; N, 7.01.

A second crop of product (0.63 g.) was obtained by extraction of the initial ethyl acetate extracts with 3 portions of 1 N sodium hydroxide, followed by further isolation as above.

EXAMPLE 27

2-(5-Methyl-2-thienyl)-2-trimethylsiloxyethanenitrile

5-Methyl-2-thenaldehyde (25 g., 0.2 mole), zinc iodide (266 mg.) and 100 ml. of ether were combined and stirred at room temperature. Trimethylsilylcarbonitrile (23.5 g., 0.24 mole) was added dropwise and the reaction mixture stirred for an additional 2 hours. The reaction mixture was diluted with 100 ml. of ether, washed with two 50 ml. portions of 5% sodium bicarbonate, washed with two 25 ml. portions of brine, dried over anhydrous magnesium sulfate, filtered and evaporated to dryness to produce 2-(5-methyl-2-thienyl)-2-trimethylsiloxyethanenitrile [42 g.; pnmr/CDCl$_3$/delta: 0.2 (s, 9H); 2.2 (s, 3H); 5.6 (s, 1H); 6.6–7.4 (m, 2H)].

EXAMPLE 28

Ethyl 1-Hydroxy-1-(5-methyl-2-thienyl)methanecarboximidate Hydrochloride

With cooling to 0°–5° C., ethanol (550 ml.) was saturated with hydrogen chloride. 2-(5-Methyl-2-thienyl)-2-trimethylsiloxyethanenitrile (42 g.) was dissolved in portions and the solution maintained at 0° C. for 2.5 hours. The reaction mixture was evaporated to dryness and the residue triturated with diethyl ether to provide ethyl 1-hydroxy-1-(5-methyl-2-thienyl)methanecarboximidate hydrochloride [33 g.; m.p. 122°–123° C., pnmr/DMSO/delta: 1.1–1.6 (3H); 2.5 (3H); 4.6 (2H); 5.9 (1H); 6.6–7.2 (2H)].

EXAMPLE 29

5-(5-Methyl-2-thienyl)oxazolidine-2,4-dione

Ethyl 1-hydroxy-1-(5-methyl-2-furyl)methanecarboximidate hydrochloride (10 g., 0.042 mole) was combined with triethylamine (14.1 g., 0.14 mole) in 250 ml. of tetrahydrofuran and cooled to 0°–5° C. The cold reaction mixture was perfused with phosgene for 30 minutes, warmed to room temperature and poured portionwise onto about 275 ml. of crushed ice. The product was extracted into two 200 ml. portions of ethyl acetate. The ethyl acetate extracts were combined and extracted with two 150 ml. portions of 1 N sodium hydroxide. The combined aqueous extracts were acidified with hydrochloric acid and then extracted with two 250 ml. portions of fresh ethyl acetate. The last, combined organic extracts were dried over anhydrous magnesium sulfate, filtered and evaporated to yield 5-(5-methyl-2-thienyl)oxazolidine-2,4-dione (7.2 g.). Recrystallization from chloroform/hexane gave purified product (910 mg.; m.p. 108°–109° C.; m/e 197).

EXAMPLE 30

2-(5-Chloro-2-thienyl)-2-trimethylsiloxyethanenitrile

5-Chlorothenaldehyde (5 g., 34 mmoles) was combined with zinc iodide (50 mg.) and 30 ml. of diethyl ether and cooled to 0° C. Trimethylsilylcarbonitrile (4.04 g., 40 mmoles) was added dropwise and the reaction mixture warmed to room temperature and stirred for 4 hours. Additional equal portions of trimethylsilylcarbonitrile and zinc iodide were added and the reaction stirred an additional 16 hours. The reaction mixture was diluted with ether, washed with two 30 ml. portions of 5% sodium bicarbonate, washed once with 30 ml. of brine, dried over anhydrous magnesium sulfate and evaporated to yield 2-(5-chloro-2-thienyl)-2-trimethylsiloxyethanenitrile as an oil [4.0 g., pnmr/CDCl$_3$/delta: 0.3 (s, 9H); 5.7 (s, 1H); 7.0 (q, 2H)].

By the same method, 3-fluoro-2-thenaldehyde, 4-fluoro-2-thenaldehyde, 5-fluoro-2-thenaldehyde, 5-fluoro-3-thenaldehyde [Gronowitz and Rosen, Chem. Ser. 1, pp. 33–43 (1971); Chem. Abstracts 75, 20080c], 4-fluoro-3-thenaldehyde, 4-methoxy-3-thenaldehyde, and 4-methylthio-3-thenaldehyde are converted, respectively, to 2-(3-fluoro-2-thienyl)-2-trimethylsiloxyethanenitrile, 2-(4-fluoro-2-thienyl)-2-trimethylsiloxyethanenitrile, 2-(5-fluoro-2-thienyl)-2-trimethylsiloxyethanenitrile, 2-(5-fluoro-3-thienyl)-2-trimethylsiloxyethanenitrile, 2-(4-fluoro-3-thienyl)-2-trimethylsiloxyethanenitrile, 2-(4-methoxy-3-thienyl)-2-trimethylsiloxyethanenitrile, 2-(4-methylthio-3-thienyl)-2-trimethylsiloxyethanenitrile.

EXAMPLE 31

Ethyl 1-(5-Chloro-2-thienyl)-1-hydroxymethanecarboximidate Hydrochloride 2-(5-Chloro-2-thienyl)-2-trimethylsiloxyethanenitrile (4 g.) was dissolved in absolute ethanol (100 ml.). The solution was cooled to 0°–5° C. and saturated with hydrogen chloride. The reaction mixture was held for 16 hours at 0° C., evaporated to dryness and triturated with ether to yield solid ethyl 1-(5-chloro-2-thienyl)-1-hydroxymethanecarboximidate hydrochloride [3 g., pnmr/DMSO/delta: 1.2 (3H); 4.2 (2H); 5.3 (1H); 6.6 (1H); 6.9 (1H); 7.4 (1H); 8.4 (1H)].

By the same method, the other nitriles of the preceding Example are converted to ethyl 1-(3-fluoro-2-thienyl)-1-hydroxymethanecarboximidate hydrochloride, ethyl 1-(4-fluoro-2-thienyl)-1-hydroxymethanecarboximidate hydrochloride, ethyl 1-(5-fluoro-2-thienyl)-1-hydroxymethanecarboximidate hydrochloride, ethyl 1-(5-fluoro-3-thienyl)-1-hydroxymethanecarboximidate hydrochloride, ethyl 1-(4-fluoro-3-thienyl)-1-hydroxymethanecarboximidate hydrochloride, ethyl 1-hydroxy-1-(4-methoxy-3-thienyl)methanecarboximidate hydrochloride and 1-hydroxy-1-(4-methylthio-3-thienylmethanecarboximidate hydrochloride.

EXAMPLE 32

5-(5-Chloro-2-thienyl)oxazolidine-2,4-dione

Ethyl 1-(5-chloro-2-thienyl)-1-hydroxymethanecarboximidate hydrochloride (3.0 g., 12 mmoles) and triethylamine (4.0 g., 39 mmoles) were combined in 90 ml. of tetrahydrofuran and cooled to 0° C. The slurry was perfused with phosgene for 30 minutes, warmed to room temperature and stirred for 16 hours. The reaction mixture was poured slowly into 100 ml. of crushed ice and product extracted into two 100 ml. portions of ethyl acetate. The combined ethyl acetate extracts were backwashed with two 50 ml. portions of water and one 50 ml. portion of saturated sodium chloride, dried over anhydrous magnesium sulfate, filtered and evaporated to a semi-solid (2.5 g.). Recrystallization from toluene provided purified 5-(5-chloro-2-thienyl)oxazolidine-2,4-dione (0.6 g., m.p. 126°–130° C.).

Analysis: Calcd. for $C_7H_4O_3NClS$: C, 38.64; H, 1.84; N, 6.44. Found: C, 38.17; H, 2.07; N, 6.91.

By the same method the other imino ethers of the preceding Example are converted to 5-(3-fluoro-2-thienyl)oxazolidine-2,4-dione, 5-(4-fluoro-2-thienyl)oxazolidine-2,4-dione, 5-(5-fluoro-2-thienyl)oxazolidine-2,4-dione, 5-(5-fluoro-3-thienyl)oxazolidine-2,4-dione, 5-(4-fluoro-3-thienyl)oxazolidine-2,4-dione, 5-(4-methoxy-3-thienyl)oxazolidine-2,4-dione and 5-(4-methylthio-3-thienyl)oxazolidine-2,4-dione.

EXAMPLE 33

2-(4-Bromo-3-thienyl)-2-trimethylsiloxyethanenitrile

4-Bromo-3-thenaldehyde (5.5 g., 29 mmoles) in 75 ml. of methylene chloride was cooled to 0°–5° C. Zinc iodide (50 mg.) was added, followed by the dropwise addition of trimethylsilylcarbonitrile (3.47 g., 35 mmoles) over a 3 minute period. The mixture was warmed to room temperature, stirred for 16 hours, washed twice with saturated sodium bicarbonate, washed with brine, dried over anhydrous magnesium sulfate, filtered and evaporated to yield 2-(4-bromo-3-thienyl)-2-trimethylsiloxyethanenitrile as an oil (7.6 g., 90%, m/e 291/289).

EXAMPLE 34

Ethyl 1-(4-Bromo-3-thienyl)-1-hydroxymethanecarboximidate 2-(4-Bromo-3-thienyl)-2-trimethylsiloxyethanenitrile (7.5 g.) in 200 ml. of ethanol, cooled in an ice bath, was perfused with hydrogen chloride for 45 minutes. After an additional 20 minutes at 0°–5° C. the reaction mixture was evaporated to dryness and triturated with ether to yield the hydrochloride salt of the product as a hygroscopic solid. The salt was taken up in a mixture of methylene chloride and saturated sodium bicarbonate. The separated methylene chloride layer was washed twice with saturated sodium bicarbonate, washed with brine, dried over anhydrous magnesium sulfate, filtered and evaporated to yield ethyl 1-(4-bromo-3-thienyl)-1-hydroxymethanecarboximidate as an oil (6.1 g., 89%, m/e 265/263).

EXAMPLE 35

5-(4-Bromo-3-thienyl)oxazolidine-2,4-dione

Ethyl 1-(4-bromo-3-thienyl)-1-hydroxymethanecarboximidate (6.0 g., 23 mmoles) and triethylamine (5.15 g., 51 mmoles) were combined in 250 ml. of tetrahydrofuran, cooled in an ice-water bath and perfused with phosgene for 35 minutes. The reaction mixture was warmed to room temperature, stirred for 1.5 hours, poured slowly over 1 liter of crushed ice, and product extracted into 3 portions of methylene chloride. The combined methylene chloride extracts were evaporated to an oil, crystallized by the addition of a small amount of ether and hexane, and triturated in about 40 ml. of ether to yield 5-(4-bromo-3-thienyl)oxazolidine-3,4-dione (3.4 g., 56%; m.p. 158°–161° C.). Recrystallization from 40 ml. of toluene afforded purified product (2.51 g.; m.p. 164°–166° C.; m/e 263/261).

Alternatively, the ether solution of the lithium derivative of 3,4-dibromothiophene is reacted with a 1.05 equivalent of alloxan according to the procedure of Example 54, yielding 5-(4-bromo-3-thienyl)-5-hydroxy-2,4,6(1H,3H,5H)-pyrimidinetrione. Following the procedure of Example 55, the latter is converted to the desired 5-(4-bromo-3-thienyl)oxazolidine-2,4-dione.

EXAMPLE 36

2-(3-Thienyl)-2-trimethylsiloxyethanenitrile

3-Thenaldehyde (10 g., 0.089 moles), zinc iodide (120 mg.) and ether (60 ml.) were combined and stirred. Trimethylsilylcarbonitrile (10.6 g., 0.107 mole) was added dropwise over 10 minutes and the reaction mixture stirred for 16 hours, diluted with 60 ml. of ether, washed with two 30 ml. portions of 5% sodium bicarbonate, washed with 30 ml. of brine, dried over anhydrous magnesium sulfate, filtered and evaporated to yield 2-(3-thienyl)-2-trimethylsiloxyethanenitrile as an oil [14.3 g., pnmr/$CDCl_3$/delta: 0.2 (9H); 5.6 (1H); 7.0–7.5 (3H)].

EXAMPLE 37

Ethyl 1-Hydroxy-1-(3-thienyl)methanecarboximidate

At 0°–5° C., 2-(3-thienyl)-2-trimethylsiloxyethanenitrile (14.3 g.) was dissolved portionwise in 500 ml. of ethanol, previously saturated with hydrogen chloride at 0°–5° C. The solution was held at 0° C. for 16 hours, and the product isolated as the hydrochloride salt by evaporation of the reaction mixture to dryness and trituration of the residue with ether. The salt was taken up in 400 ml. of chloroform and 100 ml. of saturated sodium bicarbonate. The separated chloroform layer was washed with an additional 100 ml. of saturated sodium bicarbonate, washed with brine, dried over magnesium sulfate, filtered and evaporated to yield ethyl 1-hydroxy-1-(3-thienyl)methanecarboximidate [12.5 g., pnmr/$CDCl_3$/delta: 1.0–1.3 (3H); 4.8–5.3 (2H); 5.0 (1H); 6.9–7.2 (3H); 7.3–8.0 (1H)].

EXAMPLE 38

5-(3-Thienyl)oxazolidine-2,4-dione

Ethyl 1-hydroxy-1-(3-thienyl)methanecarboximidate (12.5 g., 0.067 mole) and triethylamine (16.1 g., 0.159 mole) were combined in 600 ml. of tetrahydrofuran and cooled to 0° C. The mixture was perfused with phosgene for 30 minutes, warmed to room temperature and allowed to stand for 16 hours. The mixture was poured slowly into 600 ml. of ice and water (foaming of excess phosgene), and extracted twice with 600 ml. portions of ethyl acetate. The combined extracts were washed with two 300 ml. portions of 1 N sodium hydroxide. The combined basic extracts were acidifed with hydrochloric acid and product re-extracted into two fresh 300 ml. portions of ethyl acetate. The combined fresh extracts were dried over anhydrous magnesium sulfate, filtered and evaporated to solids (8.0 g.). Recrystallization from hot toluene gave purified 5-(3-thienyl)oxazolidine-2,4-dione (5.5 g., m.p. 133°–136° C.). A second recrystallization, from ethyl acetate/hexane, provided additional purification (first crop: 2.352 g.; m.p. 136°–138° C., m/e 183; ir (KBr): 5.5, 5.8 microns).

EXAMPLE 39

Ethyl 2-Hydroxy-2-(3-thienyl)acetate

3-Thenaldehyde (10 g., 0.089 mole) and sodium bisulfite (13.8 g., 0.133 mole) were heated at 50°–60° C., in 152 ml. of water for 2 hours, forming the bisulfite adduct in situ. The reaction mixture was cooled to 5° C., and 200 ml. of ethyl acetate was added. To the stirred, two phase system, potassium cyanide (17.4 g., 0.267 mole) in 75 ml. of water was added dropwise over 30 minutes. The reaction mixture was warmed to 20° C. and held for 1 hour. Additional potassium cyanide (5.7 g., 0.088 mole) was added and the mixture stirred an additional 10 minutes at 20° C. The layers were separated and the aqueous layer washed with 50 ml. of ethyl acetate. The combined ethyl acetate layers were washed with saturated sodium chloride, providing a clean solution of the cyanohydrin of 3-thenaldehyde in ethyl acetate.

The solution of the cyanohydrin of 3-thenaldehyde in ethyl acetate was stirred at room temperature and charged with 41.6 g. (52.7 ml., 10 equiv.) of ethanol and concentrated hydrochloric acid (15.2 ml., 0.182 mole) and the mixture refluxed for 17 hours. The reaction mixture was cooled to 25° C., washed with 100 ml. of water and then with saturated sodium bicarbonate to a pH >7.0, dried over anhydrous magnesium sulfate, treated with activated carbon, filtered and evaporated to an oil (approximately 11.5 g.) which upon addition of 46 ml. of 1:1 toluene/isooctane afforded crystalline ethyl 2-hydroxy-2-(3-thienyl)acetate (7.4 g., 45%, m.p. 55°–57° C.).

EXAMPLE 40

2-Hydroxy-2-(3-thienyl)acetamide

Ethyl 2-hydroxy-2-(3-thienyl)acetate (168 g., 0.903 mole) was slurried in 15 N ammonium hydroxide (420 ml., 6.3 moles) and heated to reflux for 2.5 hours. The resulting solution was cooled to 70° C. and toluene (840 ml.) was added. The stirred mixture was allowed to cool to 20° C. and granulated for 1 hour. Filtration, with toluene wash, gave 2-hydroxy-2-(3-thienyl)acetamide (105.9 g., 75%, m.p. 120°–126° C.). A second crop (10.3 g., m.p. 114°–120° C.) was obtained by evaporating the aqueous layer of the filtrate to 50 ml. and granulating with 100 ml. of toluene. Recrystallization of the first and second crops from ethyl acetate afforded a 77–79% recovery of purified product (m.p. 127°–130° C.).

EXAMPLE 41

5-(3-Thienyl)oxazolidine-2,4-dione

At 25° C., 2-hydroxy-2-(3-thienyl)acetamide (10.0 g., 0.064 mole) was added to a solution of sodium methoxide (10 g., 0.185 mole) and diethyl carbonate (22.0 ml., 0.182 mole) in 200 ml. of ethanol. The reaction mixture was heated to reflux for 3 hours, cooled to 20° C., and slowly diluted with 100 ml. of water. Ethanol was removed by evaporation and the aqueous residue treated with activated carbon and filtered. The filtrate was layered with ethyl acetate and the pH adjusted to 1.0 with concentrated hydrochloric acid. The aqueous layer was separated and washed with 100 ml. of ethyl acetate. The combined ethyl acetate layers were dried over anhydrous magnesium sulfate. The ethyl acetate was removed by distillation in vacuo with displacement by toluene to a final volume of 150 ml. The resulting slurry was heated to reflux (solution), cooled to 0° C., and filtered to yield 5-(3-thienyl)oxazolidine-2,4-dione (8.92 g., 76.5%, m.p. 135°–138° C.).

EXAMPLE 42

Sodium 5-(3-Thienyl)oxazolidine-2,4-dione 5-(3-Thienyl)oxazolidine-2,4-dione (3.0 g., 16.4 mmole) was dissolved in 60 ml. of ethyl acetate and treated with 300 mg. of activated carbon. After stirring at 20° C. for 10 minutes, the mixture was filtered with ethyl acetate wash. Methanolic sodium hydroxide (3.78 N, 4.2 ml.) was added and the sodium salt was allowed to crystallize. After about 30 minutes, 0.3 ml. of water was added. The slurry was granulated for 30 minutes at room temperature, then cooled to 5° C. and granulated for an additional 30 minutes. Filtration gave sodium 5-(3-thienyl)oxazolidine-2,4-dione as the monohydrate (3.37 g., 95%, m.p. 208°–210° C.).

Analysis: Calcd. for $C_7H_4NSNa.H_2O$: C, 37.67; H, 2.71; N, 6.28; O, 28.67; S, 14.37; Na, 10.30; $H_2O$, 8.07. Found: C, 37.35; H, 3.03; N, 6.24; O, 27.83; S, 14.33; Na, 10.76; $H_2O$, 8.30.

Sodium hydroxide is substituted with an equivalent of potassium hydroxide, diethanolamine, meglumine or piperazine to produce the corresponding salts. The solvent is removed by evaporation or a non-solvent such as ether or hexane is added as necessary to facilitate precipitation of the product.

The same methods are employed to produce the pharmaceutically acceptable salts of the other oxazolidine-2,4-diones of the present invention.

EXAMPLE 43

2-(3-Bromo-2-thienyl)-2-trimethylsiloxyethanenitrile

3-Bromo-2-thenaldehyde (6 g., 31 mmoles) and zinc iodide (50 mg.) were combined with 180 ml. of methylene chloride. Trimethylsilylcarbonitrile (4.0 g., 5.2 ml., 41 mmoles) were added dropwise. The reaction mixture was stirred for 24 hours at room temperature, diluted with 50 ml. of methylene chloride, washed with 60 ml. of 5% sodium bicarbonate and then with 50 ml. of brine, dried over anhydrous magnesium sulfate, filtered and evaporated to yield 2-(3-bromo-2-thienyl)-2-trimethylsiloxyethanenitrile (7.2 g., oil, m/e 291/289).

EXAMPLE 44

Ethyl 1-(3-Bromo-2-thienyl)-1-hydroxymethanecarboximidate Hydrochloride

At 0° C., 2-(3-bromo-2-thienyl)-2-trimethylsiloxyethanenitrile (7.0 g., 24 mmoles) was dissolved in 210 ml. of ethanol saturated at 0° C. with hydrogen chloride. After stirring for 30 minutes at the same temperature, the reaction mixture was evaporated to dryness. Trituration of the solid residue with ether afforded ethyl 1-(3-bromo-2-thienyl)-1-hydroxymethanecarboximidate hydrochloride (7.0 g., m.p. 120°–122° C.).

EXAMPLE 45

5-(3-Bromo-2-thienyl)oxazolidine-2,4-dione

Ethyl 1-(2-bromo-2-thienyl)-1-hydroxymethanecarboximidate hydrochloride (6.8 g., 23 mmoles) and triethylamine (7.6 g., 10.5 ml., 76 mmoles) were combined in 250 ml. of tetrahydrofuran. The mixture was cooled to 0°–5° C., perfused with phosgene for 30 minutes, warmed to room temperature, stirred for 16 hours, and poured slowly into 300 ml. of crushed ice. The quenched reaction mixture was extracted twice with 200 ml. portions of chloroform. The combined chloroform extracts were washed with 60 ml. of brine, dried over anhydrous magnesium sulfate, filtered and evaporated to an oil. Addition of hexane and ether afforded crystalline product. Recrystallization from toluene gave 5-(3-bromo-2-thienyl)oxazolidine-2,4-dione (2.25 g.; m.p. 138°–139° C.).

Analysis: Calcd. for $C_7H_4O_3NSBr$: C, 32.09; H, 1.59; N, 5.34; S, 12.21. Found: C, 32.41; H, 1.75; N, 5.49; S, 12.61.

EXAMPLE 46

5-(5-Bromo-2-thienyl)-2-thioxooxazolidin-4-one

Potassium cyanide (7.9 g., 0.123 mole) and potassium thiocyanate (10 g., 0.104 mole) were combined in 8.5 ml. of water and stirred at 0° C. 5-Bromo-2-thenaldehyde (20 g., 0.104 mole) was added, yielding a slurry. Hydrochloric acid (30%, 50.7 ml.) was added, producing an oil ball. The reaction mixture was diluted with 104 ml. of water and stirred for 48 hours, by which time a granular solid had formed. Solids were recovered by filtration and distributed between chloroform and 5% sodium bicarbonate. The mixture was filtered, and the aqueous layer separated, acidified and the precipitated product recovered by filtration. Recrystallization from toluene gave purified 5-(5-bromo-2-thienyl)-2-thiooxazolidin-4-one (2.08 g., m.p. 119°–120° C., m/e 279/277).

Analysis: Calcd. for $C_7H_4BrNO_2S_2$: C, 30.23; H, 1.95; N, 5.04. Found: C, 30.54; H, 1.72; N, 5.26.

EXAMPLE 47

5-(5-Bromo-2-thienyl)oxazolidine-2,4-dione 5-(5-Bromo-2-thienyl)-2-thioxooxazolidin-4-one (1.5 g.) was dissolved in 1:1 water:ethanol (10 ml.) at 50° C. Hydrogen peroxide (30%, 7.0 ml.) was added to the stirred solution, which became somewhat turbid. Turbidity was reduced by the addition of 1 ml. of ethanol. The mixture was heated at 70° C. for 30 minutes, cooled somewhat, diluted with 100 ml. water and extracted with chloroform. The chloroform extract was washed with two 50 ml. volumes of sodium bicarbonate. The combined aqueous extracts were clarified by filtration, acidified with hydrochloric acid to pH 1.0, and filtered to yield 5-(5-bromo-2-thienyl)oxazolidine-2,4-dione (0.51 g., 36%; m.p. 139°–139.5° C.; m/e 263/261).

Analysis: Calcd. for $C_7H_4BrNO_3S$: C, 32.08; H, 1.54; N, 5.34. Found: C, 32.16; H, 1.69; N, 5.47.

EXAMPLE 48

5-Hydroxy-5-(3-methoxy-2-thienyl)-2,4,6(1H,3H,5H)-pyrimidinetrione

3-Methoxythiophene [2.4 g., crude material prepared according to Arkiv. Kemi. 12, 239–246 (1958); Chem. Abstr. 52, 20115d] and alloxan hydrate (3.2 g.) were dissolved by heating in 25 ml. of ethanol. Hydrochloric acid (1 N, 3 ml., 3 mmoles) was added and the mixture refluxed for 3 minutes. The mixture was cooled to room temperature and diluted with 15 ml. of water to induce further crystallization of product. Filtration with 1:1 ethanol:water and then water wash gave 5-hydroxy-5-(3-methoxy-2-thienyl)2,4,6(1H,3H,5H)-pyrimidinetrione [1.5 g., m.p. 190°–210° C. (dec.); $R_f$ 0.3 (1:1 hexane:ethyl acetate with 5% acetic acid); m/e 256].

EXAMPLE 49

5-(3-Methoxy-2-thienyl)oxazolidine-2,4-dione

5-Hydroxy-5-(3-methoxy-2-thienyl)-2,4,6(1H,3H,5H)-pyrimidinetrione (1 g.) was dissolved in 1 N sodium hydroxide (20 ml.) and stirred for 1 hour. The mixture was acidified, clarified, extracted twice with 50 ml. portions of ethyl acetate. The combined ethyl acetate extracts were back-washed with water and evaporated to dryness (0.5 g. of solids). Chromatography on about 85 ml. of silica gel, monitored by tlc, afforded 5-(3-methoxy-2-thienyl)oxazolidine-2,4-dione (300 mg., m.p. 156°–158° C.).

Analysis: Calcd. for $C_8H_7O_4NS$: C, 45.08; H, 3.31; N, 6.57. Found: C, 45.21; H, 3.39; N, 6.47.

EXAMPLE 50

5-Hydroxy-5-(5-phenyl-2-furyl)-2,4,6(1H,3H,5H)-pyrimidinetrione

2-Phenylfuran (5.76 g., 40 mmoles) was combined with 100 ml. of tetrahydrofuran and cooled to −30° C. Butyl lithium in hexane (2.3 M, 19.1 ml.) was added dropwise over 5 minutes, keeping the temperature between −20° and −30° C. The reaction mixture was allowed to warm to room temperature and then recooled to −30° C. Sublimed alloxan (5.96 g., 42 mmoles) in 40 ml. of tetrahydrofuran was added over 5 minutes, again keeping the temperature −20° to −30° C. The reaction mixture was again allowed to warm to room temperature, then recooled to 0° C. and 50 ml. of 1 N hydrochloric acid added portionwise over 2–3 minutes. The quenched reaction mixture was extracted with 100 ml. of ethyl acetate. The extract was filtered through a bed of anhydrous magnesium sulfate, and evaporated to yield 5-hydroxy-5-(5-phenyl-2-furyl)-2,4,6(1H,3H,5H)-pyrimidinetrione [9.4 g., gummy solid, $R_f$ 0.75 (1:1 hexane ethyl acetate/5% acetic acid)] contaminated with starting material ($R_f$ 0.45).

EXAMPLE 51

5-(5-Phenyl-2-furyl)oxazolidine-2,4-dione

5-Hydroxy-5-(5-phenyl-2-furyl)-2,4,6(1H,3H,5H)pyrimidinetrione (0.7 g.) was dissolved in 15 ml. of 1 N sodium hydroxide, stirred at room temperature for 15 minutes, extracted with ethyl acetate, made slightly acidic with about 1 ml. of glacial acetic acid, and extracted with 25 ml. of ethyl acetate. The latter ethyl acetate extract was back washed with about 6.5 ml. of water, filtered over a bed of anhydrous magnesium sulfate and evaporated to yield solid 5-(5-phenyl-2-furyl)oxazolidine-2,4-dione [100 mg.; m.p. 216°–218° C.; $R_f$ 0.6 (1:1 hexane:ethyl acetate/5% acetic acid)].

EXAMPLE 52

5-Hydroxy-5-(5-methyl-2-furyl)-2,4,6(1H,3H,5H)pyrimidinetrione

2-Methylfuran (3.28 g., 3.58 ml., 40 mmoles) was combined with 100 ml. of tetrahydrofuran. The reaction mixture, flushed with nitrogen, was cooled to −30° C. and butyl lithium (19.1 ml. of 2.3 M in hexane) was added over a period of 10 minutes, maintaining the temperature at −20° to −30° C. The reaction mixture was warmed to room temperature and then back to −30° C. Sublimed alloxan (5.96 g.) in 40 ml. of tetrahydrofuran was added dropwise over 10 minutes, keeping the temperature at −20° to −30° C. The reaction mixture was warmed to room temperature, cooled to 0° C. and 50 ml. of 1 N hydrochloric acid added portionwise, keeping the temperature at 0° to 5° C. The reaction mixture was extracted with 100 ml. of ethyl acetate. The extract was back washed with 25 ml. of water, filtered through a bed of anhydrous magnesium sulfate and evaporated to yield solid 5-hydroxy-5-(5-methyl-2-furyl)-2,4,6(1H,3H,5H)-pyrimidinetrione (6.3 g.; m/e 224).

EXAMPLE 53

5-(5-Methyl-2-furyl)oxazolidine-2,4-dione

5-Hydroxy-5-(5-methyl-2-furyl)-2,4,6(1H,3H,5H)pyrimidinetrione (6.3 g.) was dissolved in 50 ml. of 1 N sodium hydroxide and stirred at room temperature for 15 minutes. The reaction mixture was extracted with 50 ml. of ethyl acetate, and acidified with glacial acetic acid. Product was then extracted into fresh ethyl acetate (three 30 ml. portions). The combined ethyl acetate extracts were filtered through a bed of anhydrous magnesium sulfate and evaporated to an oil. The oil was chromatographed on 50 ml. of silica gel, with 1:1 hexane:ethyl acetate/5% acetic acid as eluant. The column was monitored by tlc using the same eluant. Clean product containing fractions were combined, evaporated to dryness and triturated with hexane (311 mg., m.p. 135°–138° C.). Recrystallization from methanol/water afforded purified 5-(5-methyl-2-furyl)oxazolidine-2,4-dione (142 mg., m.p. 136.5°–137.5° C.).

Analysis: Calcd. for $C_8H_7NO_4$: C, 53.04; H, 3.90; N, 7.73. Found: C, 52.82; H, 4.03; N, 7.65.

EXAMPLE 54

5-Hydroxy-5-(3-thienyl)-2,4,6(1H,3H,5H)pyrimidinetrione

Isopropyl ether (40 ml.) was cooled to −70° C. Butyl lithium in hexane (2.4 M, 10 ml., 24 mmoles) was added over 10 minutes, keeping the temperature −70° to −60° C. 3-Bromothiophene (1.9 ml., 20 mmoles) was added over 20 minutes, keeping the temperature −72° to −68° C. The mixture was stirred for an additional 30 minutes at −72° to −70° C. Sublimed alloxan (3 g., 21 mmoles) in 25 ml. of tetrahydrofuran was added over 40 minutes, keeping the temperature −70° to −65° C. Stirring at this temperature was continued for 15 minutes. The cooling bath was removed and the reaction mixture stirred for one hour at room temperature, then cooled to 5° C. Hydrochloric acid (1 N, 40 ml.) was added slowly, and the organic phase separated. The aqueous phase was extracted with 35 ml. of ethyl acetate. The combined organic phase/extract was washed with 10 ml. of water, dried over anhydrous sodium sulfate and concentrated to yield solid 5-hydroxy-5-(3-thienyl)-2,4,6(1H,3H,5H)pyrimidinetrione (1.41 g., 31%; m/e 226).

When this reaction was carried out in tetrahydrofuran with reverse addition of the 3-bromothiophene to butyl lithium, with immediate addition of 0.5 equivalent of alloxan hydrate in place of 1 equivalent of anhydrous alloxan, the product was a mixture of the above trione and 5-(3-bromo-2-thienyl)-5-hydroxy-2,4,6(1H,3H,5H)pyrimidinetrione, which in turn was converted to a mixture of 5-(3-bromo-2-thienyl)oxazolidine-2,4-dione and 5-(3-thienyl)oxazolidine-2,4-dione by the method of Example 55.

EXAMPLE 55

5-(3-Thienyl)oxazolidine-2,4-dione

5-Hydroxy-5-(3-thienyl)-2,4,6(1H,3H,5H)pyrimidinetrione (1.16 g., 5.1 mmoles) was dissolved in 1 N sodium hydroxide (11 ml., 11 mmoles) and allowed to stand at room temperature for 15 minutes. The solution was acidified with acetic acid, and product allowed to crystallize over 35 minutes. Filtration gave 5-(3-thienyl)oxazolidine-2,4-dione (480 mg., 51%; m.p. 133°–135° C.). An additional crop of product was obtained by extracting the mother liquor with ethyl acetate. The extract was back washed with water, and evaporated to dryness (80 mg., contaminated with starting material).

EXAMPLE 56

5-(3-Furyl)-5-hydroxy-2,4,6(1H,3H,5H)pyrimidinetrione

The detailed procedure of Example 54, but substituting 3-bromofuran (2.94 g., 1.8 ml., 20 mmoles) for the 3-bromothiophene, was employed to produce 5-(3-furyl)-5-hydroxy-2,4,6(1H,3H,5H)pyrimidinetrione (1.62 g., oil, m/e 210).

EXAMPLE 57

5-(3-Furyl)oxazolidine-2,4-dione 5-(3-Furyl)-5-hydroxy-2,4,6(1H,3H,5H)pyrimidinetrione (1.62 g.) was dissolved in 15 ml. of 1 N sodium hydroxide, and allowed to stand for 15 minutes at room temperature, and then extracted with 5 ml. of ethyl acetate. The aqueous layer was acidified with glacial acetic acid (about 1.5 ml.) and product extracted into 25 ml. of ethyl acetate. The extract was back washed with 5 ml. of water, filtered through a bed of anhydrous sodium sulfate, and evaporated to yield crude product as an oil (470 mg., m/e 167). Crystallization from chloroform gave purified 5-(3-furyl)oxazolidine-2,4-dione (129 mg., m.p. 88°–90° C., m/e 167). A second, lower melting crop was obtained from mother liquor.

EXAMPLE 58

3-Thenaldehyde Cyanohydrin

Sodium bisulfite (30.2 g., 0.29 mole) was dissolved in 190 ml. of water and warmed to 50° C. 3-Thenaldehyde (25 g., 0.22 mole) was added and the reaction mixture held at 50°–55° C. for 35 minutes, by which time all but a small amount of gummy solids were in solution. The mixture was cooled to 5° C. and layered with 190 ml. of isopropyl ether. With stirring, sodium cyanide (24.8 g., 0.25 mole) in 190 ml. of water was added dropwise over 20 minutes, keeping the temperature below 10° C. Stirring was continued at room temperature for 1 hour. The organic layer was separated, and the aqueous phase extracted with fresh isopropyl ether (300 ml.). The combined organic extracts were washed with brine, dried over anhydrous magnesium sulfate, filtered and concentrated to yield 3-thenaldehyde cyanohydrin as an oil (28.3 g., 92%).

EXAMPLE 59

2-Hydroxy-2-(3-thienyl)acetamide

Formic acid (0.5 ml.) was cooled in an ice-water bath. 3-Thenaldehyde cyanohydrin (1.0 g.) and then concentrated hydrochloride acid (0.5 ml.) were added. The reaction mixture was stirred at room temperature for 1 hour, poured over crushed ice, and extracted with three portions of ethyl acetate. The combined extracts were washed with brine, dried over anhydrous magnesium sulfate, filtered and concentrated to an oil, which partially crystallized on scratching. Recrystallization from ethyl acetate gave 2-hydroxy-2-(3-thienyl)acetamide (389 mg., 35%, m.p. 123°–126° C., m/e 157).

EXAMPLE 60

Mixed Methyl/Ethyl Esters of 2-Benzoyl-2-(3-thienyl)malonic Acid

Commercially available mixed esters of 2-(3-thienyl)-malonic acid (47% diethyl, 43% methyl/ethyl, 10% dimethyl; 11.4 g.) were added portionwise to a dispersion of sodium hydride in oil (50%, 2.4 g.) slurried in 70 ml. of toluene. An exotherm was noted, the temperature rising to 45° C. The reaction mixture was stirred for 3 hours at room temperature, and then cooled in an ice-water bath. Benzoyl peroxide (8 g.) in 100 ml. of toluene was added over a period of 1 hour, maintaining the temperature 10°–20° C. The mixture was stirred for 30 minutes at room temperature, diluted dropwise with 50 ml. of water (initial foaming noted), and finally diluted with 50 ml. of ether. The organic phase was separated, back washed with three 25 ml. portions of water, and evaporated to yield mixed methyl/ethyl esters of 2-benzoyloxy-2-(3-thienyl)malonic acid as an oil (15.5 g. containing about 1.2 g. of oil from the sodium hydride dispersion).

EXAMPLE 61

5-(3-Thienyl)oxazolidine-2,4-dione

Sodium (0.46 g., 20 mmoles) was dissolved in 50 ml. of absolute ethanol. To the resulting warm solution of sodium ethoxide (about 60° C.), crude mixed esters of 2-benzoyloxy-2-(3-thienyl)malonic acid (7 g., approximately 20 mmoles, as prepared in Example 60) were added, followed by urea (1.2 g., 20 mmoles) dissolved in 20 ml. of hot ethanol. The reaction mixture was heated in an oil bath at 105°–110° C. for 4.5 hours. The reaction mixture was cooled, acidified with concentrated hydrochloric acid, and extracted with ethyl acetate. The extract was back washed with water and concentrated to an oil. Trituration with 20 ml. of 1:1 ether:hexane gave a mixture of 5-(3-thienyl)oxazolidine-2,4-dione and intermediate 5-benzoyloxy-5-(3-thienyl)2,4,6(1H,3H,5H-)pyrimidinetrione (0.8 g.). A portion of this mixture (0.3 g.) was dissolved in 1 N sodium hydroxide (5 ml.) and allowed to stand for 20 minutes at room temperature. The reaction mixture was clarified by filtration, and acidified with acetic acid to precipitate 5-(3-thienyl)oxazolidine-2,4-dione (100 mg., m.p. 136°–138° C.).

EXAMPLE 62

2-(3-Benzo[b]thienyl)-2-trimethylsiloxyethanenitrile

Benzo[b]thiophene-3-carbaldehyde [1.8 g., 11 mmoles, J. Chem. Soc. C., pp. 339–340 (1969)] and about 100 mg. of zinc iodide were combined in 35 ml. of ether. Trimethylsilylcarbonitrile (1.98 g., 20 mmoles) was added dropwise. After approximately 1 hour, the reaction mixture was washed in sequence with saturated sodium bicarbonate, water and brine, dried over anhydrous sodium sulfate, filtered and evaporated to yield 2-(3-benzo[b]thienyl)-2-trimethylsiloxyethanenitrile [2.5 g., oil, $R_f$ 0.7 (1:2 ethyl acetate:hexane)].

EXAMPLE 63

Ethyl 1-(3-Benzo[b]thienyl)-1-hydroxymethanecarboximidate Hydrochloride

With cooling in an ice-water bath, 2-(3-benzo[b]-thienyl)-2-trimethylsiloxyethanenitrile (2.3 g.) was dissolved in 10 ml. of saturated ethanolic hydrogen chloride, and held for 16 hours at about 5° C. The reaction mixture was evaporated to dryness and triturated with ether to yield 1-(3-benzo[b]thienyl)-1-hydroxymethanecarboximidate hydrochloride (2.2 g., m.p. 128°–131° C., m/e 235).

EXAMPLE 64

5-(3-Benzo[b]thienyl)oxazolidine-2,4-dione

Ethyl 1-(3-benzo[b]thienyl)-1-hydroxymethanecarboximidate hydrochloride (2.36 g., 8.7 mmoles) and triethylamine (2.64 g., 26 mmoles) were combined in 50 ml. of tetrahydrofuran and cooled to 10° C. Phosgene was bubbled through the cooled reaction mixture for 30 minutes, followed by a 10 minute flush with nitrogen. The reaction mixture was slowly poured into 100 ml. of ice and extracted twice with ether. The combined ether extracts were back-washed with water and then brine, dried over anhydrous sodium sulfate, filtered, and evaporated to yield a gummy solid (1.7 g.). This crude product was dissolved in 1 N sodium hydroxide, washed twice with ether and acidified with 6 N hydrochloric acid, affording purified 5-(3-benzo[b]thienyl)oxazolidine-2,4-dione (950 mg., m.p. 202°–205° C., m/e 233).

Analysis: Calcd. for $C_{11}H_7O_3NS$: C, 56.64; H, 3.02; N, 6.00. Found: C, 56.74; H, 3.18; N, 5.69.

EXAMPLE 65

2-(7-Benzo[b]thienyl)-2-trimethylsiloxyethanenitrile

Benzo[b]thiophene-7-carbaldehyde [1.3 g., 8 mmoles, J. Org. Chem. 39, 2829 (1974)] was dissolved in 35 ml. of ether. Trimethylsilylcarbonitrile (1.5 ml., 12 mmoles) and zinc iodide (about 50 mg.) were added and the mixture stirred for 1 hour at room temperature, at which time tlc indicated conversion was complete. The reaction mixture was evaporated to dryness, yielding 2-(7-benzo[b]thienyl)-2-trimethylsiloxyethanenitrile [2.2 g., oil; $R_f$ 0.6 (1:5 ethyl acetate:hexane/5% acetic acid)].

EXAMPLE 66

Ethyl 1-(7-Benzo[b]thienyl)-1-hydroxymethanecarboximidate Hydrochloride

By the procedure of Example 63, 2-(7-benzo[b]-thienyl)-2-trimethylsiloxyethanenitrile (2.1 g.), using 35 ml. of saturated ethanolic hydrogen chloride, was converted to ethyl 1-(7-benzo[b]thienyl-1-hydroxymethanecarboximidate hydrochloride (1.1 g., m.p. 120°–122° C.), after crystallization from acetone.

EXAMPLE 67

5-(7-Benzo[b]thienyl)oxazolidine-2,4-dione

Following the procedure of Example 64, ethyl 1-(7-benzo[b]thienyl)-1-hydroxymethanecarboximidate hydrochloride (1.1 g., 4 mmoles) and triethylamine (1.7 ml., 12 mmoles) were reacted with phosgene. The crude product, isolated as an oil, was dissolved in 25 ml. ether and product extracted into 50 ml. of 1 N sodium hydroxide. This aqueous extract was acidified with concentrated hydrochloric acid and product extracted into fresh ether, which was back washed with water and evaporated in vacuo to a solid residue (670 mg.). This residue was recrystallized to yield 5-(7-benzo[b]thienyl-)oxazolidine-2,4-dione (0.45 g., m.p. 130°–132° C.).

Analysis: Calcd. for $C_{11}H_7O_3NS$: C, 56.64; H, 3.02; N, 6.00. Found: C, 56.42; H, 3.18; N, 5.91.

EXAMPLE 68

5-Hydroxy-5-(5-methoxy-2-thienyl)-2,4,6(1H,3H,5H)-pyrimidinetrione

2-Methoxythiophene (2.3 g., 20 mmoles) was dissolved in 35 ml. of ether. With cooling, butyl lithium in hexane (2.4 M, 9 ml., 21.6 mmoles) was added dropwise over 15 minutes, the temperature rising as high as 35° C. during this addition. The reaction mixture was stirred for 1 hour at room temperature. While maintaining the temperature between $-20°$ and $-15°$ C., sublimed alloxan (3 g., 21 mmoles) in 20 ml. of tetrahydrofuran was added during 10 minutes. The mixture was warmed to room temperature, stirred for 0.5 hour, cooled to 5° C. and quenched by adding 35 ml. of 1 N hydrochloric acid in portions. The organic phase was separated and the aqueous phase extracted with 25 ml. of ethyl acetate. The combined organic phase and extract were back-washed with water, concentrated to dryness and triturated with hexane to yield solid 5-hydroxy-5-(5-methoxy-2-thienyl)-2,4,6(1H,3H,5H)-pyrimidinetrione (1.4 g., m/e 256).

EXAMPLE 69

5-(5-Methoxy-2-thienyl)oxazolidine-2,4-dione

5-Hydroxy-5-(5-methoxy-2-thienyl)-2,4,6(1H,3H,5H)-pyrimidinetrione (1.1 g.) was dissolved in 10 ml. of 1 N sodium hydroxide, allowed to stand for 1.5 hours at room temperature, extracted with ether, acidified with acetic acid, diluted with 15 ml. of water and filtered to yield product [567 mg., m.p. 144°–146° C. (dec.)]. Recrystallation from acetone-hexane gave purified 5-(5-methoxy-2-thienyl)oxazolidine-2,4-dione in two crops [487 mg., m.p. 147°–148° C. (dec.)].

Analysis: Calcd. for $C_8H_7O_4NS$: C, 45.08; H, 3.31; N, 6.57. Found: C, 45.08; H, 3.41; N, 6.39.

EXAMPLE 70

5-[5-(2-phenyl-1,3-dioxolan-2-yl)-2-thienyl]-2,4,6(1H,3H,5H)-pyrimidinetrione

At room temperature, 2-phenyl-2-thienyl)-1,3-dioxolane (3.26 g., 14 mmoles) was dissolved in 35 ml. of ether. Butyl lithium in hexane (2.4 M, 6.25 ml., 15 mmoles) was added dropwise over 15 minutes, the temperature rising to 33° C. The mixture was stirred for 75 minutes at room temperature and then cooled. Maintaining the temperature between $-15°$ and $-20°$ C., sublimed alloxan (2.13 g., 15 mmoles) in 20 ml. of tetrahydrofuran was added dropwise over 10 minutes. The reaction mixture was stirred at room temperature for 30 minutes, cooled to 5° C., quenched with 35 ml. of 1 N hydrochloric acid, added in small portions, and extracted with 25 ml. of ethyl acetate. The organic layer was back washed with 15 ml. of water, filtered through a bed of anhydrous sodium sulfate, and evaporated to yield 5-[5-(2-phenyl-1,3-dioxolan-2-yl)thienyl]-2,4,6(1H,3H,5H)-pyrimidinetrione [oil, $R_f 0.25$ (1:1 hexane:ethyl acetate/5% acetic acid)] contaminated with starting material ($R_f 0.8$).

EXAMPLE 71

5-[5-(2-Phenyl-1,3-dioxolan-2-yl)-2-thienyl]oxazolidine-2,4-dione

The entire crude product from the preceding Example was taken into 35 ml. of 1 N sodium hydroxide and allowed to stand for 30 minutes. After acidification the product was extracted into isopropyl ether. The extract was back washed with water and evaporated to yield 5-[5-(2-phenyl-1,3-dioxolan-2-yl)thienyl]oxazolidine-2,4-dione [0.40 g., $R_f 0.65$ (1:1 ethyl acetate:hexane/5% acetic acid)].

EXAMPLE 72

5-(5-Benzoyl-2-thienyl)oxazolidine-2,4-dione

5-[5-(2-Phenyl-1,3-dioxolan-2-yl)-2-thienyl]oxazolidine-2,4-dione (0.40 g.) was dissolved in 30 ml. of ether and stirred with 10 ml. of 6 N hydrochloric acid at room temperature for 1 hour. Ethyl acetate (10 ml.) was added, and the organic layer was separated and evaporated in vacuo to dryness (0.388 g.). Chromatography on 50 ml. of silica gel, eluted with 1:1 hexane:ethyl acetate/5% acetic acid and monitored by tlc, gave in early fractions purified 5-(5-benzoyl-2-thienyl)oxazolidine-2,4-dione (0.22 g., m.p. 153°–155° C., m/e 287).

Analysis: Calcd. for $C_{14}H_9O_4NS$: C, 58.52; H, 3.16; N, 4.87. Found: C, 58.69; H, 3.50; N, 4.94.

EXAMPLE 73

5-(3-Thienyl)oxazolidine-2,4-dione Capsules

The following ingredients were combined and blended for 30 minutes:

Sodium 5-(3-thienyl)oxazolidine-2,4-dione monohydrate: 30.46*
Lactose, anhydrous, U.S.P.: 14.05 g.
Corn starch, dried, U.S.P.: 5.00 g.
*Equivalent to 25 g. of active drug (unsolvated free acid).

The mixture was milled (0.040 inch plate) and blended for an additional 30 minutes. Magnesium stearate, sodium lauryl sulfate, 90/10 blend (1.00 g.) was added and the mixture blended for 20 minutes. The blend was filled into #0 gelatin capsules (505 mg. fill weight) so as to obtain capsules of 250 mg. potency.

Larger capsules are employed to prepare capsules of higher potency.

The same procedure was employed to prepare capsules of 100 mg. potency from the following ingredients:

Sodium 5-(3-thienyl)oxazolidine-2,4-dione monohydrate: 12.18 g.*
Lactose, anhydrous, U.S.P.: 32.32 g.
Corn starch, dried, U.S.P.: 5.00 g.
Magnesium stearate/lauryl sulfate (90/10 blend): 0.50 g.
*Equivalent to 10 g. of activated ingredient (unsolvated free acid).

A lower level of active ingredient in the blend is used to prepare capsules of lower potency.

EXAMPLE 74

Tablets

A tablet base is prepared by blending the following ingredients in the proportion by weight indicated:

Sucrose, U.S.P.: 80.3
Tapioca starch: 13.2
Magnesium stearate: 6.5

Into this tablet base there is blended sufficient sodium 5-(3-thienyl)oxazolidine-2,4-dione monohydrate to form tablets containing 50 mg., 100 mg. or 250 mg. of active drug (weight equivalent to the free acid). The portion of blend to active drug is within the limits of 1-0.167 to 1-1, e.g., in the extremes, 60.2 mg. of sodium salt monohydrate and 300 mg. of blend in a 50 mg. tablet or 304.6 mg. of sodium salt monohydrate and 250 mg. of blend in a 250 mg. tablet.

EXAMPLE 75

Injectable Preparation

Sterile sodium 5-(3-thienyl)oxazolidine-2,4-dione is dry filled into vials so as to contain 670.1 mg. of the sodium salt monohydrate per vial (equivalent to 550 mg. of free acid). Prior to use, sterile water for injection (11 ml.) is added, and the mixture shaken to form a solution, containing 50 mg./ml. of active drug, which is suitable for intravenous, intramuscular or subcutaneous injection.

Alternatively vials are filled by a freeze drying procedure. Two ml. of a sterile, aqueous solution containing 335 mg./ml. of sodium salt monohydrate is introduced into each vial. The vials are freeze dried on trays.

EXAMPLE 76

3-Ethoxycarbonyl-5-(3-thienyl)oxazolidine-2,4-dione

Sodium 5-(3-thienyl)oxazolidine-2,4-dione monohydrate is stripped of water by drying in vacuo at elevated temperature (50°-70° C.). The anhydrous salt (2.05 g., 10 mmoles) is suspended in 35 ml. of 1,2-dichloroethane. Ethyl chloroformate (1.41 g., 10 mmoles) is added and the mixture refluxed for about 2 hours. The reaction mixture is cooled to room temperature, by-product sodium chloride removed by filtration and the filtrate concentrated to dryness to yield 3-ethoxycarbonyl-5-(3-thienyl)oxazolidin-2,4-dione.

Substitution of the ethyl chloroformate with an equivalent quantity of acetyl chloride, isobutyryl chloride, N,N-dimethylcarbamoyl chloride, or benzoyl chloride produces, respectively, 3-acetyl-5-(3-thienyl)oxazolidine-2,4-dione, 3-isobutyroyl-5-(3-thienyl)oxazolidine-2,4-dione, 3-(N,N-dimethylcarbamoyl)-5-(3-thienyl)oxazolidine-2,4-dione and 3-benzoyl-5-(3-thienyl)oxazolidine-2,4-dione.

EXAMPLE 77

3-Acetyl-5-(3-thienyl)oxazolidine-2,4-dione

Method A 5-(3-Thienyl)oxazolidine-2,4-dione (1.83 g., 10 mmoles) and triethylamine (0.14 ml., 10 mmoles) are combined with 25 ml. of 1,2-dichloroethane at room temperature. Acetyl chloride (0.72 ml., 10 mmoles) is added dropwise over a few minutes and the reaction mixture stirred for 3 hours. The reaction mixture is evaporated to dryness and the residue distributed between saturated sodium bicarbonate and chloroform. The chloroform layer is washed with water, and then brine, dried over anhydrous magnesium sulfate, filtered and evaporated to yield 3-acetyl-5-(3-thienyl)oxazolidine-2,4-dione.

Method B 5-(3-Thienyl)oxazolidine-2,4-dione (1.83 g., 10 mmoles) and acetic anhydride (1.14 ml., 12 mmoles) are combined with 20 ml. of tetrahydrofuran and stirred for 40 hours. The reaction mixture is evaporated to dryness and 3-acetyl-5-(3-thienyl)oxazolidine-2,4-dione further isolated as in Method A.

The same procedure, but substituting acetic anhydride with an equivalent of acetoformic acid reagent [a solution of acetic-formic anhydride in acetic acid; cf. Blackwood et al., J. Am. Chem. Soc., 82, 5194 (1960)], propionic anhydride or benzoic anhydride, allows formation of corresponding 3-formyl-5-(3-thienyl)oxazolidine-2,4-dione, 3-propionyl-5-(3-thienyl)oxazolidine-2,4-dione and 3-benzoyl-5-(3-thienyl)oxazolidine-2,4-dione.

EXAMPLE 78

3-(N-Methylcarbamoyl)-5-(3-thienyl)oxazolidine-2,4-dione 5-(3-Thienyl)oxazolidine-2,4-dione (1.83 g., 10 moles) and one drop of triethylamine are combined in 35 ml. of 1,2-dichloroethane. Methyl isocyanate (0.58 ml., 10 mmoles) is then added and the reaction mixture stirred for 4 hours at room temperature. The reaction is diluted with 35 ml. of 1,2-dichloroethane, washed with saturated sodium bicarbonate and then brine, dried over magnesium sulfate, filtered and concentrated to yield 3-(N-methyl)-5-(3-thienyl)oxazolidine-2,4-dione.

EXAMPLE 79

3-(4-Methoxy-3-thienyl)-2-trimethylsiloxyethanenitrile

By the procedure of Example 1, 4-methoxy-3-thenaldehyde (2.6 g., 18.3 mmole) and trimethylsilylcarbonitrile (2.15 g., 21.7 mmole) in 250 ml. of ether in the presence of 50 mg. of zinc iodide was converted to title product as an oil (3.9 g., m/e 241).

EXAMPLE 80

Methyl 1-Hydroxy-1-(4-methoxy-3-thienyl)methanecarboximidate Hydrochloride

Saturated methanolic hydrogen chloride (100 ml.) was maintained at 0°-5° C. in an ice bath. Title product of the preceding Example (3.9 g.) in 20 ml. of methanol was added dropwise and the mixture held for 1 hour at 0°-5° C. The reaction mixture was concentrated to solids and the residue triturated with ether to yield the title product [2.76 g., m.p. 94°-99° C. (dec.)]. Recrystallization from methanol-ether gave purified title product [1.51 g.; m.p. 112-114 (dec.); m/e 201].

EXAMPLE 81

5-(4-Methoxy-3-thienyl)oxazolidine-2,4-dione

By the procedure of Example 3, the product of the preceding Example (1.3 g., 5.5 mmoles) and triethylamine (1.7 g., 17 mmoles) in 50 ml. of tetrahydrofuran were reacted with phosgene for 30 minutes at 0°-5° C. The reaction mixture was stirred overnight at room temperature. The reaction mixture was poured slowly into 500 ml. of crushed ice and extracted with three 50 ml. portions of chloroform. The combined organic layers were washed with brine, dried over anhydrous magnesium sulfate, filtered and concentrated to solids. Recrystallization from toluene gave purified title product [510 mg.;

m.p. 120°–122° C.; ir (KBr) 1377, 1732, 1767, 1808 cm$^{-1}$].

Analysis: Calcd. for C$_8$H$_7$O$_4$NS: C, 45.06; H, 3.31; N, 6.57. Found: C, 45.31; H, 3.41; N, 6.85.

EXAMPLE 82

3-(4-Ethoxy-3-thienyl)-2-trimethylsiloxyethanenitrile

By the procedure of Example 1, 4-ethoxy-3-thenaldehyde (8.1 g., 0.052 mole) and trimethysilylcarbonitrile (6.13 g., 0.062 mole) in 300 ml. of ether, in the presence of 50 mg. of zinc iodide, were converted to title product (13 g.) as a viscous oil; pnmr indicated absence of the aldehyde proton.

EXAMPLE 83

Ethyl 1-Hydroxy-1-(4-ethoxy-3-thienyl)methanecarboximidate Hydrochloride

Using ethanol in place of methanol, but otherwise the procedure of Example 80, product of the preceding Example (13 g.) was converted to title compound [9.23 g., m.p. 126°–128° (dec.)].

EXAMPLE 84

5-(4-Ethoxy-2-thienyl)oxazolidine-2,4-dione

Using a phosgene perfusion time of 1 hour at 0°–5° C. and a further reaction time of 1 hour at room temperature, product of the preceding Example (9.2 g.) was converted to title product. To isolate the product, the reaction was poured in 1.5 l. of crushed ice and extracted with three 200 ml. portions of chloroform. The organic layers were combined and extracted with three 150 ml. portions of 1 N sodium hydroxide. The basic extracts were combined, back-washed with 200 ml. of fresh chloroform, reacidified with 3 N hydrochloric acid and extracted with three 200 ml. portions of chloroform. The last three organic extracts were combined, washed with brine, dried over magnesium sulfate, filtered, evaporated to solids, and the residue crystallized from toluene to yield title compound [4.06 g., m.p. 144°–146° C., m/e 227; ir (KBr) 1822, 1737, 1568 cm$^{-1}$].

Analysis: Calcd. for C$_9$H$_9$O$_4$NS: C, 47.57; H, 3.99; N, 6.17 Found: C, 47.18; H, 4.04; N, 6.06.

The chloroform back-wash was reextracted with three 150 ml. portions of fresh 1 N sodium hydroxide. These basic extracts were combined and additional product (980 mg., m.p. 144°–146° C.) recovered in like manner.

EXAMPLE 85

2-[4-(n-Propoxy)-3-thienyl]-2-trimethylsiloxyethanenitrile

By the procedure of Example 1, 4-(n-propoxy)-3-thenaldehyde (3.1 g., 18 mmoles) and trimethylsilylcarbonitrile (2.28 g., 2.9 ml., 23 mmoles) in 250 ml. of ether, in the presence of 50 mg. of zinc iodide, were converted to title product as an oil [4.6 g.; m/e 269; ir (CH$_2$Cl$_2$) 2936, 1558 cm$^{-1}$].

EXAMPLE 86

Ethyl 1-Hydroxy-1-[4-(n-propoxy)-3-thienyl]methanecarboximidate Hydrochloride

Using a reaction time of 20 minutes after completion of the addition, the procedure of Example 83 was used to convert the product of the preceding Example (4.5 g.) into title product of the present Example [3.05 g., m.p. 127°–129° C. (dec.)].

EXAMPLE 87

5-[4-(n-Propoxy)-3-thienyl]oxazolidine-2,4-dione

By the procedure of Example 81, the product of the preceding Example (2.8 g., 0.01 mole) was converted to toluene recrystallized 5-[4-(n-propoxy)-3-thienyl]oxazolidine-2,4-dione [1.63 g.; m.p. 134°–136° C.; m/e 241; ir (KBr) 1827, 1747, 1564 cm$^{-1}$].

EXAMPLE 88

2-(4-Methoxy-2-methyl-3-thienyl)-2-trimethylsiloxyethanenitrile

By the procedure of Example 1, 4-methoxy-2-methyl-3-thenaldehyde (5.2 g., 33.3 mmoles) and trimethylsilylcarbonitrile (3.96 g., 40 mmoles) in 350 ml. of ether, in the presence of 50 mg. of zinc iodide, were converted to title product, isolated as a viscous oil [7.3 g.; m/e 255; ir (CH$_2$Cl$_2$) 1575, 1204, 1075 cm$^{-1}$].

EXAMPLE 89

Ethyl 1-Hydroxy-1-(4-methoxy-2-methyl-3-thienyl)methanecarboximidate Hydrochloride The procedure of Example 83 was applied to the product of the preceding Example (7.2 g.) to produce 5.8 g. of a mixture of title compound and the corresponding ethoxy ether (estimated by pnmr to be about 40% methyl ether and 60% ethyl ether; showing both m/e 243 and 229).

A portion of this mixture (2.5 g.) was taken into 100 ml. of methanol, cooled to 0°–5° C., and perfused with hydrogen chloride for 1 hour. After 1 hour additional stirring at 0° C., the reaction mixture was evaporated to a viscous oil. Crystallization from ether gave title product [2.1 g.; m.p. 123°–125° C. (dec.); m/e 229].

The corresponding methyl imidate ester of the title product is obtained by directly reacting the product of the preceding Example with methanolic hydrogen chloride according to the procedure of Example 80.

EXAMPLE 90

Ethyl 1-(Hydroxy)-1-(4-Ethoxy-2-methyl-3-thienyl)methanecarboximidate Hydrochloride A portion of the mixed methyl and ethyl ethers of the preceding Example (2.5 g.) was taken into 100 ml. of ethanol and cooled to 0° C. The cold solution was perfused with hydrogen chloride for 1 hour, stirred for an additional hour at 0° C. and evaporated to an oil. The oil was crystallized by trituration with ether. Repulping in ether gave title product [2.07 g., m.p. 105°–107° C. (dec.); m/e 243].

EXAMPLE 91

5-(4-Methoxy-2-methyl-3-thienyl)oxazolidine-2,4-dione

Using a reaction time of 3.5 hours at room temperature, but otherwise following the procedure of Example 3, the product of Example 89 (2.0 g., 7.5 mmoles) was converted to toluene recrystallized title product [0.52 g., m.p. 179°–181° C.; m/e 227; ir (KBr) 1820, 1750, 1727, 1583 cm$^{-1}$].

EXAMPLE 92

5-(4-Ethoxy-2-methyl-3-thienyl)oxazolidine-2,4-dione

By the procedure of the preceding Example, the product of Example 90 (1.9 g.) was converted to title product [245 mg., m.p. 136°–138° C.; m/e 241; ir (KBr) 1824, 1743 cm$^{-1}$].

EXAMPLE 93

5-Hydroxy-(2,5-Dimethyl-3-furyl)-2,4,6(1H,3H,5H)pyrimidinetrione

Isopropyl ether (35 ml.) was cooled to −68° C. Butyl lithium (5 ml. of 2.1 M in hexane, 10.5 mmoles) was added, allowing the temperature to rise to −60° C. 2,5-Dimethyl-3-iodofuran [J. Am. Chem. Soc. 70, p. 739 (1948); 1.2 ml, 9 mmoles] was then added dropwise keeping the temperature between −65° and −68° C. After stirring for 0.5 hour at −68° C., anhydrous alloxan (1.5 g., 10.6 mmoles) dissolved in 15 ml. of tetrahydrofuran was added dropwise over 30 minutes, keeping the temperature −65° to −60° C. The stirred reaction mixture was warmed over 15 minutes to 0° C., 1 N hydrochloric acid (25 ml.) was added and the organic phase separated. The aqueous phase was extracted with 20 ml. of ethyl acetate. The combined organic layers were washed with 10 ml. of water and evaporated to yield title product [1 g., R$_f$0.05 (1:5 ethyl acetate:hexane/5% acetic acid)].

EXAMPLE 94

5-(2,5-Dimethyl-3-furyl)oxazolidine-2,4-dione

Product of the preceding Example (1 g.) was taken into 10 ml. of 1 N sodium hydroxide and held for 15 minutes. The solution was extracted with 5 ml. of ethyl acetate, acidified with acetic acid and extracted with 25 ml. of ethyl acetate. The acidic extract was back-washed with 5 ml. of water and evaporated to solids (340 mg.), which were chromatographed on 50 ml. of silica gel, using 1:1 ethyl acetate:hexane as eluant and tlc monitoring. Clean fractions were combined, evaporated to dryness and the residue recrystallized from ether-hexane to yield purified title product [170 mg.; m.p. 144°–145°; m/e 195; R$_f$0.3 (1:5 ethyl acetate:hexane/5% acetic acid); R$_f$0.55 (1:1 ethyl acetate:hexane)].

Analysis: Calcd. for C$_9$H$_9$O$_4$N: C, 55.38; H, 4.65; N, 7.18 Found: C, 55.15; H, 4.76; N, 7.04.

EXAMPLE 95

5-Hydroxy-5-(4-iodo-3-furyl)-2,4,6(1H,3H,5H)pyrimidinetrione 3,4-Diiodofuran (0.96 g., 3 mmoles) in 5 ml. of ether was added slowly to a cold (−65° C.) solution of butyl lithium (2 ml. of 2.3 M in hexane, 4.6 mmoles) in 15 ml. of ether. The mixture was stirred for 20 minutes at −65° C. Anhydrous alloxan (0.57 g., 4 mmoles) was dissolved in 10 ml. of tetrahydrofuran and added slowly to the 4-iodo-3-furyl lithium solution at −65° C. After 10 minutes at the same temperature, the reaction mixture was warmed to 15° C., acidified with 15 ml. of 1 N hydrochloric acid and extracted with ether. The ether extract was back-washed with 10 ml. of water, concentrated to dryness and the residue triturated with 2 ml. of hexane to yield title product [108 mg.; m/e 336; R$_f$0.5 (1:1 ethyl acetate:hexane/5% acetic acid)].

EXAMPLE 96

5-(4-Iodo-3-furyl)oxazolidine-2,4-dione

Product of the preceding Example (100 mg.) was allowed to stand with 1 ml. of 1 N sodium hydroxide for 15 minutes at room temperature. The reaction mixture was acidified with acetic acid and extracted with 3 ml. of ethyl acetate. The organic extract was backwashed with 1 ml. of water and evaporated to a gum (63 mg.). Crude material (120 mg.) prepared in this manner was chromatographed on 50 ml. of silica gel using 1:1 ethyl acetate:hexane as eluant and tlc monitoring. The first fractions from the column were combined and evaporated to a gum (78 mg. which crystallized from chloroform to yield purified title product (45 mg.; m.p. 140°–144° C.).

Analysis: Calcd. for C$_7$H$_4$O$_4$NI: C, 28.69; H, 1.38; N, 4.78. Found: C, 28.37; H, 1.62; N, 4.74.

EXAMPLE 97

2-(5-Chloro-2,3-dihydro-7-benzo[b]furanyl)-2-trimethylsiloxyethanenitrile

5-Chloro-2,3-dihydrobenzo[b]furan-7-carbaldehyde (900 mg., 4.9 mmoles) was dissolved in 25 ml. of ether. Zinc iodide (20 mg.) and then trimethylsilylcarbonitrile (970 mg., 9.8 mmoles) were added and the mixture stirred 16 hours at room temperature, then diluted with 50 ml. ether, washed with three portions of saturated sodium bicarbonate and one of brine, dried over anhydrous magnesium sulfate, filtered and evaporated to yield title product as an oil [1.4 g.; m/e 283/281; ir (CHCl$_2$) 1479, 1457, 1435, 1180, 866, 848 cm$^{-1}$].

By the same method 5-fluoro-2,3-dihydrobenzo[b]furan-7-carbaldehyde is converted to 2-(5-fluoro-2,3-dihydro-7-benzo[b]furanyl)-2-trimethylsiloxyethanenitrile.

EXAMPLE 98

Ethyl 1-(5-Chloro-2,3-dihydro-7-benzo[b]furanyl)-1-hydroxymethanecarboximidate Hydrochloride By the procedure of Example 83, title compound of the preceding Example (1.37 g.) was converted to title product. The initially isolated solids were repulped twice in ether to obtain purified product [1.28 g.; m.p. 149°–152° C. (dec.); m/e 257/255; ir (KBr) 3162, 2875, 1650, 1524, 1458 cm$^{-1}$].

By the same method the fluoro compound of the preceding Example is converted to ethyl 1-(5-fluoro-2,3-dihydro-7-benzo[b]furanyl)-1-hydroxymethanecarboximidate hydrochloride.

EXAMPLE 99

5-(5-Chloro-2,3-dihydro-7-benzo[b]furanyl)oxazolidine-2,4-dione

By the procedure of Example 84, title compound of the preceding Example (1.1 g.) was converted to toluene recrystallized title product [630 mg.; m.p. 197°–199° C.; m/e 255/253; ir (KBr) 3084, 1833, 1810, 1746 cm$^{-1}$].

By the same procedure the fluoro analog of the preceding Example is converted to 5-(5-fluoro-2,3-dihydro-7-benzo[b]furanyl)oxazolidine-2,4-dione.

EXAMPLE 100

5-(5-Chloro-7-benzo[b]furanyl]oxazolidine-2,4-dione

Title product of the preceding Example (100 mg., 0.39 mmole) was suspended in 6 ml. of chloroform and bis(trimethylsilyl)trifluoroacetamide (100 mg., 0.104 ml., 0.39 mmole) added in one portion. After stirring for 1 minute, N-bromosuccinimide (69 mg., 0.39 mmole) was added together with a trace (a single crystal) of benzoyl peroxide. The mixture was heated to reflux for 2 hours, cooled to room temperature, filtered from insolubles and evaporated to semisolids under a stream of nitrogen. The residue was partitioned between 1 N sodium hydroxide and ethyl acetate. The aqueous layer was separated, washed with fresh ethyl acetate, acidified with 1 N hydrochloric acid and extracted with three portions of chloroform. The chloroform extracts were combined, dried over anhydrous magnesium sulfate, filtered, concentrated to an oil, and title product crystallized from toluene (44 mg.; m.p. 154°–157° C.; m/e 251.253).

By the same method the fluoro analog of the preceding Example is converted to 5-(5-fluoro-7-benzo[b]furanyl]oxazolidine-2,4-dione.

PREPARATION 1

3-Furaldehyde

3-Furylmethanol (19.6 g., 0.2 mole) in 50 ml. of methylene chloride was added dropwise to a slurry of pyridinium chlorochromate (64.5 g., 0.3 mole) in 450 ml. of methylene chloride. The exothermic reaction, which led to vigorous reflux, was controlled by occasional cooling with an ice-bath. By the end of 60 minutes, gummy solids had precipitated. The reaction mixture was diluted with 600 ml. of ether and the supernatant separated by a combination of decantation and filtration. The filtrate was passed through Florisil (synthetic magnesium silicate) contained in a short column, with ether as eluant. Collected fractions were combined and evaporated to an oil. Distillation of the oil provided 3-furaldehyde (7.6 g.; b.p. 68°–72° C./40–45 nm.).

Alternatively, this aldehyde is prepared by Rosenmund reduction of 3-furoic acid chloride [Hayes, J. Am. Chem. Soc. 71, 2581 (1949)].

PREPARATION 2

2-(2-Furyl)-1,3-dioxolane

2-Furaldehyde (42 ml., 0.5 mole), ethyleneglycol (50 ml., 0.9 moles) and p-toluenesulfonic acid (about 200 mg.) were combined in 150 ml. of toluene and the mixture refluxed for 6 hours while collecting byproduct water in a Dean-Stark trap. The mixture was cooled, diluted with 500 ml. of ether, and clarified by filtration. The filtrate was washed with 200 ml. of saturated sodium bicarbonate and the organic phase again clarified by filtration. This second filtrate was washed with 200 ml. of water, and the organic layer concentrated to dryness, affording 2-(2-furyl)-1,3-dioxolane as an oil (45 g.).

PREPARATION 3

2-(5-Chloro-2-furyl)-1,3-dioxolane 2-(2-Furyl)-1,3-dioxolane (14 g., 0.1 mole) was dissolved in 100 ml. of tetrahydrofuran and the solution cooled to −25° to −20° C. Maintaining this temperature range, butyl lithium in hexane (45 ml. of 2.2 M, 0.1 mole) was added over a period of 10 minutes. The mixture was allowed to warm to 0° C. over 25 minutes and rechilled to −30° C. While maintaining a temperature range of −30° C. to −25° C., hexachloroethane (23.7 g., 0.1 mole) in 50 ml. of tetrahydrofuran was added over 5 minutes. The reaction mixture was warmed to room temperature, stirred for 1.5 hours, recooled to 5° C., and diluted slowly with 500 ml. of water. Product was extracted into ether (2×500 ml.) and recovered as an oil (15.8 g.) by evaporation to dryness. The oil was chromatographed on a 200 ml. volume of silica gel, using 8:1 hexane:ethyl acetate as eluant and monitoring by silica gel tlc with the same eluant. The early, product containing fractions were combined with evaporated to yield purified 2-(5-chloro-2-furyl)-1,3-dioxolane as an oil [5 g.; $R_f$ 0.6 (8:1 hexane:ethyl acetate)].

PREPARATION 4

5-Chloro-2-furaldehyde 2-(5-Chloro-2-furyl)-1,3-dioxolane (4.8 g.) was dissolved in 20 ml. of ether. 6 N Hydrochloric acid (10 ml.) was added and the two-phase mixture stirred for 1 hour at room temperature. The ether phase was separated, washed with water and evaporated to yield 5-chloro-2-furaldehyde as an oil (2.8 g.).

PREPARATION 5

5-Bromo-2-furylcarboxamide

5-Bromo-2-furoic acid (20 g.) was refluxed for 3 hours with 60 ml. of thionyl chloride, and the corresponding acid chloride isolated as an oil by concentration. The acid chloride was added dropwise to 150 ml. of stirring, concentrated ammonium hydroxide. Filtration afforded 5-bromo-2-furylcarboxamide (17.0 g., m.p. 140°–143° C.).

PREPARATION 6

5-Bromo-2-furylcarbonitrile

5-Bromo-2-furylcarboxamide (10 g.) was combined with 50 ml. of phosphorus oxychloride and refluxed for 24 hours. The mixture was poured onto ice, the product extracted into ether, which on evaporation gave 5-bromo-2-furylcarbonitrile as an oil (6.4 g.).

PREPARATION 7

5-Bromo-2-furaldehyde

5-Bromo-2-furylcarbonitrile (2.3 g., 13 mmoles) was dissolved in 50 ml. of ether and cooled, under nitrogen, to −10° C. Diisobutylaluminum hydride (1.9 g., 13 mmoles) as a 25% solution in toluene was added dropwise, maintaining the temperature near −10° C. The reaction was allowed to warm to room temperature and allowed to stir about 6 hours. The reaction mixture was cooled to 0° to 5° C., diluted with 1 ml. of methanol, acidified with 3 N hydrochloric acid, washed with water, and evaporated to yield 5-bromo-2-furaldehyde (1.2 g., m.p. 74°–76° C.).

PREPARATION 8

3-Bromo-2-furaldehyde

Phosphorus oxychloride (6.5 g., 70 mmoles) was added to dimethylformamide (5.4 g., 70 mmoles) at 0° to 10° C. The resulting slurry was diluted with 10 ml. of ethylene dichloride. Maintaining the mixture near 10° C., 3-bromofuran (9.2 g., 63 mmoles) was added. The reaction mixture was then heated to 58°–60° C. for 1 hour and then recooled to 10° C. Sodium acetate trihydrate (15 g.) dissolved in 25 ml. of water was added slowly, with good stirring, keeping the temperature 10° to 30° C. The mixture was reheated to 68°–72° C. for 20 minutes, cooled to room temperature, and diluted with 20 ml. of water. Product was extracted into 75 ml. of ether, and the ether back-washed with water and concentrated to yield 3-bromo-2-furaldehyde as an oil [0.9 g., $R_f$ 0.65 (3:1 hexane:ethyl acetate)].

PREPARATION 9

3-Iodofuran

3-Bromofuran (14.7 g., 0.1 mole) in 100 ml. of ether was cooled to −70° C. Butyl lithium (42 ml. of 2.4 M, 0.1 mole) in hexane was added dropwise over 0.5 hour, maintaining the temperature from −70° to −65° C. Iodine (25 g., 0.1 mole) in 200 ml. of ether was then added over 1 hour maintaining the same temperature range. The reaction mixture was warmed to room temperature and then back to 2° C. Water (100 ml.) was added dropwise. The ether layer was separated, washed with aqueous thiosulfate and then water, dried over anhydrous sodium sulfate, evaporated to an oil and distilled to yield 3-iodofuran (15.7 g., b.p. 48°/28 mm.).

PREPARATION 10

3-Methoxyfuran

Sodium metal (5.6 g., 0.24 mole) was dissolved in 150 ml. of dry methanol. 3-Iodofuran (15.7 g., 0.08 mole) and cuprous oxide (8 g., 0.1 mole) were added and the mixture was refluxed with vigorous stirring for 42 hours. The reaction mixture was cooled to room temperature, diluted with 200 ml. of water, and product extracted into 100 ml. of ether. The ether extract was back-washed with 15 ml. of water, dried over anhydrous sodium sulfate and evaporated to yield crude 3-methoxyfuran (approximately 3–4 g. of approximately 50% purity) suitable for further processing.

PREPARATION 11

5-Phenyl-2-thenaldehyde

1-Phenylthiophene [1.6 g., 0.01 mole, prepared according to J. Am. Chem. Soc. 46, 2339 (1924)] was dissolved in 20 ml. of tetrahydrofuran and cooled to −40° C. Butyl lithium in hexane (4.5 ml. of 2.2 M) was added over 3 minutes, maintaining the temperature −40° to −30° C. The mixture was warmed to 0° C. and then cooled to −40° C. Dimethylformamide (1.2 ml., 15 mmole) was added, maintaining the temperature −40° to −30° C. The mixture was warmed to room temperature and held for 0.5 hour, recooled to 0° C., quenched with 6 ml. of 6 N hydrochloric acid, diluted with 10 ml. of water, and extracted with 20 ml. of ether. Evaporation of the ether extract to dryness gave crude product (1.9 g.). Recrystallization from about 35 ml. of hexane gave purified 5-phenyl-2-thenaldehyde (0.9 g., m.p. 90°–92° C.).

PREPARATION 12

4-Bromo-3-thenaldehyde 3,4-Dibromothiophene [15 g., 0.062 mole, J. Org. Chem. 36, 2690 (1971)] in 20 ml. of ether was cooled to −70° C. and butyl lithium in hexane (34.8 ml. of 2.1 M, 0.073 mole) added dropwise over 5 minutes. After stirring for 5 minutes at −70° C., the solution was transferred, via nylon tubing under nitrogen pressure, to a solution of dimethylformamide (6.8 g., 0.093 mole) in 35 ml. of ether. The resulting mixture was heated to reflux for 2 hours, cooled to room temperature, washed in sequence with two portions of 1 N hydrochloric acid, one of saturated sodium bicarbonate and one of brine, dried over anhydrous magnesium sulfate, filtered and concentrated to an oil. The oil was twice distilled to yield 4-bromo-3-thenaldehyde (5.7 g., b.p. 81°–84° C./0.8 mm., m/e 192/190).

PREPARATION 13

2-Phenylfuran

Aniline (46.5 g., 0.5 mole) was combined with 500 ml. of water and 100 ml. of concentrated hydrochloric acid and cooled to −5° C. Sodium nitrite (36.2 g., 0.525 mole) in 100 ml. of water was added dropwise over 45 minutes, keeping the temperature −3° to −5° C. After addition was complete, the mixture was stirred for 30 minutes at −5° C., and zinc chloride (68 g.) was added. Maximal precipitation of the diazonium salt was obtained by the addition of 100 g. of sodium chloride. The mixture was stirred for 5 minutes, with the cooling bath removed and cautiously filtered, without wash, and air dried for 2 hours. (Previous vacuum drying of this product led to explosive decomposition). The intermediate diazonium salt was suspended in 750 ml. of furan at 0° C. With vigorous stirring, powdered sodium hydroxide (5 g.) was added, followed by anhydrous sodium acetate (10 g.). The reaction mixture was stirred for 5 hours at 0° C. and then for 16 hours at room temperature. Solids were removed by filtration and the filtrate evaporated to crude product (25 ml. of oil). Distillation afforded 1-phenylfuran (9.2–9.6 g., b.p. 87°–95°/15 mm., b.p. 50°/1 mm.).

PREPARATION 14

2-Phenyl-2-(2-thienyl)-1,3-dioxolane

2-Benzoylthiophene (19 g., 0.1 mole), ethylene glycol (11 ml., 0.2 mole), toluene (150 ml.) and p-toluenesulfonic acid (about 0.2 g.) were combined and refluxed for 6 hours. By-product water was collected in a Dean-Stark trap. Tlc (1:8 ethyl acetate:hexane) indicated reaction to be about 40% complete. More ethylene glycol (30 ml.) was added and reflux continued for 35 hours. Reaction was still incomplete. The reaction mixture was diluted with 200 ml. of ether, washed twice with 150 ml. portions of water and concentrated to dryness. The residue was chromatographed on about 500 ml. of silica gel, with 1:8 ethyl acetate:hexane as eluant, monitored by tlc. Faster moving, product containing fractions were combined and evaporated to yield 2-phenyl-2-(2-thienyl)-1,3-dioxolane [8 g., oil, $R_f$ 0.6 (1:8 ethyl acetate:hexane)].

PREPARATION 15

Methyl 4-Methoxy-3-thenoate

Methyl 4-acetoxy-3-thenoate (U.S. Pat. No. 3,144,235; 10 g.) was dissolved in 20 ml. of methanol and added to 100 ml. of methanol containing 0.31 ml. of concentrated sulfuric acid. The mixture was refluxed for 4 days, then neutralized with 0.6 g. of sodium acetate and solvent removed by evaporation. The residue was taken up in 200 ml. of ether. The ether solution was washed sequentially with two 50 ml. portions of water, two 50 ml. portions of 1 N sodium hydroxide and two 50 ml. portions of brine, dried over anhydrous magnesium sulfate, filtered and evaporated to an oil which crystallized on standing (4.35 g.; m.p. 64°–66° C.).

When this reaction was worked up after only 1 day only a low yield of the desired product (2.2 g) was isolated. The two 1 N sodium hydroxide extracts were combined and acidified, precipitating methyl 4- hydroxy-3-thenoate (5.13 g.). When this alcohol was dissolved in 100 ml. of methanol containing 0.3 ml. of concentrated sulfuric acid and refluxed for 3 days, the above work-up afforded title product (2.10 g., m.p. 64°–66° C.).

PREPARATION 16

1-(4-Methoxy-3-thienyl)methanol

Methyl 4-methoxy-3-thenoate (U.S. Pat. No. 4,144,235; 3.9 g., 23 mmoles) was dissolved in 50 ml. of toluene and cooled in an acetone-dry ice bath. Diisobutyl aluminum hydride (46 ml. of 1 M in hexane, 46 mmoles) was added dropwise over 30 minutes. The mixture was stirred for an additional 2 hours at the bath temperature and then allowed to warm to room temperature. Keeping the temperature below 30° C., methanol (14.7 g., 18.6 ml., 0.46 mole) was slowly added. The mixture was then stirred for 16 hours at room temperature, by which time a granular precipitate had formed. The mixture was filtered over diatomaceous earth with methanol wash. The combined filtrate and washes were concentrated to yield the title product as an oil (2.8 g., m/e 144).

PREPARATION 17

4-Methoxy-3-thenaldehyde

Pyridinium chlorochromate (6.4 g., 29.7 mmoles) was dissolved in 100 ml. of methylene chloride and added in one portion to a solution of the product of the preceding Example (2.8 g., 19.8 mmoles) also in 100 ml. of methylene chloride. The reaction mixture was stirred at room temperature for three hours, diluted with 200 ml. of ether and decanted from the black precipitate. The precipitate was washed with two 100 ml. portions of ether. The combined decant and washes were filtered, washed in sequence with two portions of 1 N hydrochloric acid, one portion of water, two portions of 1 N sodium hydroxide and one portion of brine, dried over anhydrous magnesium sulfate, filtered and concentrated to yield title product as an oil [2.6 g.; m/e 142; ir (CH$_2$Cl$_2$) 1688, 1544 cm$^{-1}$].

PREPARATION 18

Ethyl 4-Ethoxy-3-thenoate

Following the approximate procedure of U.S. Pat. No. 4,144,235, methyl 4-acetoxy-3-thenoate (20 g.) was dissolved in 240 ml. of ethanol and 0.62 ml. of concentrated sulfuric acid was added. The reaction mixture was gently refluxed for 79 hours, then neutralized with sodium acetate (1.2 g.) and evaporated to an oil. The latter was partitioned between 400 ml. of ether and 50 ml. of water. The organic layer was separated and washed in sequence with 75 ml. of water, three 50 ml. portions of 1 N sodium hydroxide and two 75 ml. portions of brine, dried over anhydrous magnesium sulfate, filtered and evaporated to yield title product as an oil [14.9 g., pnmr indicates entirely ethyl ester, no methyl ester].

PREPARATION 19

1-(4-Ethoxy-3-thienyl)methanol

By the procedure of Preparation 16, the product of the preceding Preparation (14 g.) was converted to title product as an oil (9.15 g.).

PREPARATION 20

4-Ethoxy-3-thenaldehyde

By the procedure of Preparation 17, the product of the preceding Preparation (9.15 g.) was converted to the title product, initially isolated as an oil which quickly crystallized on cooling [8.18 g.; m.p. 42°–45° C.; m/e 156; ir (KBr) 3090, 2977, 1688 cm$^{-1}$].

PREPARATION 21 n-Propyl 4-(n-Propoxy)-3-thenoate

By the procedure of Preparation 18, using a reaction reflux time of 10 days, methyl 4-acetoxy-3-thenoate (6 g.) in 750 ml. of 1-propanol containing 0.19 ml. of concentrated sulfuric acid was converted to title product as an oil (5.4 g.; m/e 228).

PREPARATION 22

1-[4-(n-Propoxy)-3-thienyl]methanol

By the procedure of Preparation 16, the product of the preceding Preparation (5.4 g.) was reduced to title compound, isolated as an oil (3.44 g.; m/e 172).

PREPARATION 23

4-(n-Propoxy)-3-thenaldehyde)

By the procedure of Preparation 17, the product of the preceding Preparation (3.34 g.) was converted to title compound [3.19 g.; m/e 170; ir (CH$_2$Cl$_2$) 1689, 1539 cm$^{-1}$].

PREPARATION 24

Ethyl 4-Methoxy-2-methyl-3-thenoate

Ethyl 4-hydroxy-2-methyl-3-thenoate [Chem. Ber. 48, p. 593 (1915); 7.8 g.] was combined with 600 ml. of methanol and 0.25 ml. concentrated sulfuric acid and refluxed for 21 hours. The reaction mixture was evaporated to an oil, taken up in 500 ml. of ether, washed with two 50 ml. portions of 1 N sodium hydroxide and then one of brine, dried over anhydrous magnesium sulfate, and evaporated to yield title product as an oil (7.8 g.; m/e 200; pnmr/CDCl$_3$ includes singlet OCH$_3$ protons at 3.9 ppm). The product is contaminated with a minor portion of the corresponding methyl ester.

PREPARATION 25

(4-Methoxy-2-methyl-3-thienyl)methanol

The product of the preceding Preparation (7.8 g., 0.039 mol) was dissolved in 100 ml. of hexane and 75 ml. of toluene and cooled to −78° C. Diisobutyl aluminum hydride (78 ml. of 1 M in hexane, 0.078 mole) was added dropwise over 40 minutes. The mixture was stirred for 2 hours at −78° C., warmed to room temperature and stirred for an additional 16 hours. Methanol (25.0 g., 31.6 ml., 0.78 mole) was added dropwise to the reaction mixture, keeping the temperature below 30° C. After stirring 1.5 hours at room temperature, the reaction mixture was clarified by filtration over diatomaceous earth, with thorough methanol wash and repulp of the cake and finally methylene chloride wash. The combined filtrate and washes were dried over anhydrous magnesium sulfate, filtered and evaporated to yield title product as an oil (5.56 g.; m/e 158; ir (CH$_2$Cl$_2$) 3598, 1582, 1708 cm$^{-1}$).

PREPARATION 26

4-Methoxy-2-methyl-3-thenaldehyde

By the procedure of Preparation 17, the product of the preceding Preparation (5.4 g., 0.034 mole) was converted to title compound isolated as an oil [5.23 g.; $R_f$ 0.36 (chloroform)].

PREPARATION 27

5-Chlorobenzo[b]furan-2-carboxylic Acid

5-Chlorosalicylaldehyde (31.3 g., 0.2 mole) was dissolved in 200 ml. of 2-butanone. Potassium carbonate (82.9 g., 0.6 mole) and then diethyl 2-bromomalonate (95.6 g., 0.4 mole) were added and the mixture heated to reflux for five hours, then cooled, filtered from salts, and concentrated to an oil. The oil was partitioned between 500 ml. of 10% sulfuric acid and 500 ml. of ether. The aqueous layer was extracted with two 250 ml. portions of fresh ether. The combined organic layers were washed with brine, dried over anhydrous magnesium sulfate, filtered and concentrated to a second oil. The second oil was dissolved in 400 ml. of 10% ethanolic potassium hydroxide, heated at reflux for 1 hour and concentrated to solids. The solids were dissolved in 1500 ml. of water, filtered from trace insoluble matter, acidified with 6 N hydrochloric acid and precipitated solids recovered by filtration. Purified title product was obtained by repulping the solids in 1 liter of water (19 g., m.p. 259°–262° C., m/e 198/196).

By the same procedure, 5-fluorosalicylaldehyde is converted to 5-fluorobenzo[b]furan-2-carboxylic acid.

PREPARATION 28

5-Chlorobenzo[b]furan

Title compound of the preceding Preparation (7.8 g.) was combined with copper powder (700 mg.) and quinoline (50 ml.) and the mixture heated to reflux for 50 minutes, then cooled to room temperature and diluted with 500 ml. of ether. Insolubles were removed by filtration and the filtrate washed in sequence with five 200 ml. portions of 2 N hydrochloric acid and one of brine, dried over anhydrous magnesium sulfate and concentrated to an oil (6.2 g.). The oil was chromatographed through 200 g. of silica gel, using ether as eluant and 300 ml. fractions. Fractions 1 and 2 were combined and evaporated to yield title product as an oil (6.1 g.).

By the same procedure the other product of the preceding Example is converted to 5-fluorobenzo[b]furan.

PREPARATION 29

5-Chloro-2,3-dihydrobenzo[b]furan

Pd/C (5%, 12.2 g.) in 400 ml. of acetic acid was prehydrogenated at atmospheric pressure and 25° C. Title compound of the preceding Preparation (6.1 g.) in 100 ml. of acetic acid was added and hydrogenation continued until slightly more than 1 equivalent of hydrogen had been consumed. Catalyst was recovered by filtration over diatomaceous earth. The filtrate was neutralized with saturated potassium carbonate and extracted with four 200 ml. portions of ether. The combined extracts were washed with brine, dried over anhydrous magnesium sulfate, filtered and evaporated to an oil. The oil was chromatographed on 400 g. of silica gel using hexane-3% ether as eluant, 15 ml. fractions and tlc monitoring. Pure product fractions 70–90 were combined and evaporated to yield title product [2.15 g.; oil; $R_f$ 0.32 (hexane); m/e 156/154].

By the same procedure the other benzofuran of the preceding Preparation is converted to 5-fluoro-2,3-dihydrobenzo[b]furan.

PREPARATION 30

5-Chloro-2,3-dihydrobenzo[b]furan-7-carbaldehyde

Title compound of the preceding Preparation (2.1 g.) in 20 ml. of methylene chloride was cooled in an ice water bath. Titanium tetrachloride (2 molar equivalents) was added, followed by the addition of 1,1-dichloromethyl methyl ether (1.05 molar equivalents). The reaction mixture was stirred at 0° for 30 minutes, then slowly poured into 100 ml. of saturated sodium bicarbonate. The aqueous phase was extracted with three fresh portions of methylene chloride. The combined organic layers were washed with brine, dried over anhydrous magnesium sulfate, filtered and evaporated to yield crude title product contaminated with an isomeric aldehyde. Purified title product was obtained by digesting the crude product in 50 ml. of boiling hexane, filtering and cooling the filtrate [0.93 g.; m.p. 79°–81° C.; $R_f$ 0.55 (chloroform); m/e 184/182].

By the same method the 5-fluoro compound of the preceding Preparation is converted to 5-fluoro-2,3-dihydrobenzo[b]furan-7-carbaldehyde.

I claim:

1. A compound of the formula

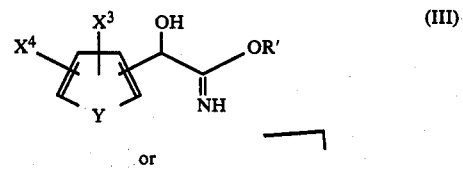

or

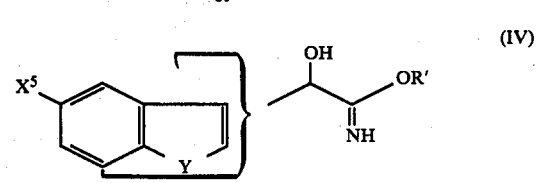

wherein
R' is lower alkyl;
Y is sulfur or oxygen;
$X^3$ is hydrogen, fluoro, chloro, bromo, iodo, methyl, phenyl or $(C_1-C_3)$-alkoxy;
$X^4$ is hydrogen or methyl; and
$X^5$ is hydrogen, fluoro, chloro, bromo or iodo;
or an acid addition salt thereof.

2. A compound of claim 1 wherein R' is ethyl.
3. A compound of claim 2 wherein Y is sulfur.
4. A compound of claim 3 having the formula (III).
5. The compound of claim 4 having the formula

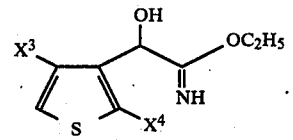

wherein $X^3$ is hydrogen, fluoro, chloro, bromo, iodo or $(C_1-C_3)$-alkoxy.

6. The compound of claim 4 having the formula

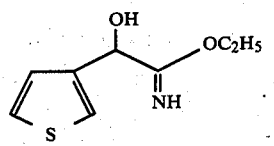

7. The compound of claim 4 having the formula

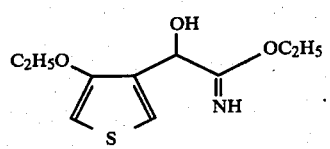

8. The compound of claim 4 having the formula

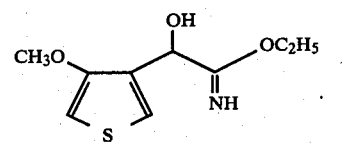

9. A compound of claim 3 having the formula (IV).

10. The compound of claim 9 having the formula

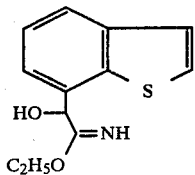

11. A compound of claim 2 wherein Y is oxygen.
12. A compound of claim 11 having the formula (III).
13. The compound of claim 12 having the formula

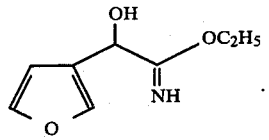

14. The compound of claim 12 having the formula

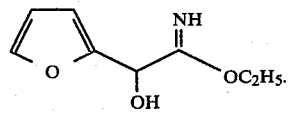

15. A compound of claim 12 having the formula

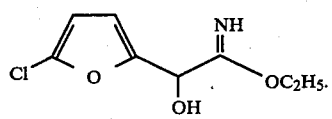

16. The compound of claim 15 having the formula

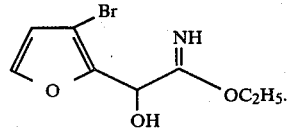

* * * * *